United States Patent
Gu et al.

(10) Patent No.: US 9,919,002 B2
(45) Date of Patent: Mar. 20, 2018

(54) METHODS AND CONSTRUCTS FOR COMPOUND DELIVERY

(71) Applicant: North Carolina State University, Raleigh, NC (US)

(72) Inventors: Zhen Gu, Apex, NC (US); Ran Mo, Raleigh, NC (US); Tianyue Jiang, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 15/031,151

(22) PCT Filed: Oct. 20, 2014

(86) PCT No.: PCT/US2014/061334
§ 371 (c)(1),
(2) Date: Apr. 21, 2016

(87) PCT Pub. No.: WO2015/061206
PCT Pub. Date: Apr. 30, 2015

(65) Prior Publication Data
US 2016/0263137 A1 Sep. 15, 2016

Related U.S. Application Data

(60) Provisional application No. 61/893,450, filed on Oct. 21, 2013.

(51) Int. Cl.
| | | |
|---|---|---|
| A61K 31/70 | (2006.01) | |
| A61K 31/704 | (2006.01) | |
| A61K 48/00 | (2006.01) | |
| A61K 9/127 | (2006.01) | |
| A61K 9/51 | (2006.01) | |
| A61K 45/06 | (2006.01) | |
| A61K 31/136 | (2006.01) | |
| A61K 31/7105 | (2006.01) | |
| A61K 38/19 | (2006.01) | |
| C12N 15/115 | (2010.01) | |
| C12N 5/00 | (2006.01) | |

(52) U.S. Cl.
CPC ............ *A61K 31/704* (2013.01); *A61K 9/127* (2013.01); *A61K 9/1273* (2013.01); *A61K 9/51* (2013.01); *A61K 9/5123* (2013.01); *A61K 9/5138* (2013.01); *A61K 9/5161* (2013.01); *A61K 9/5192* (2013.01); *A61K 31/136* (2013.01); *A61K 31/7105* (2013.01); *A61K 38/191* (2013.01); *A61K 45/06* (2013.01); *A61K 48/00* (2013.01); *C12N 15/115* (2013.01); *C12N 2310/16* (2013.01); *C12N 2320/31* (2013.01); *C12N 2320/32* (2013.01)

(58) Field of Classification Search
None
See application file for complete search history.

(56) References Cited

U.S. PATENT DOCUMENTS

| | | |
|---|---|---|
| 3,932,657 A | 1/1976 | Rahman |
| 4,356,167 A | 10/1982 | Kelly |
| 4,839,111 A | 6/1989 | Huang |
| 5,122,368 A | 6/1992 | Greenfield et al. |
| 5,804,568 A | 9/1998 | Rubinfeld |
| 6,404,710 B1 | 6/2002 | Ichimura et al. |
| 7,244,449 B2 | 7/2007 | Slater et al. |
| 7,390,780 B2 | 6/2008 | Huang et al. |
| 7,465,753 B2 | 12/2008 | Yazawa et al. |
| 7,588,778 B2 | 9/2009 | Kan et al. |
| 7,763,420 B2 | 7/2010 | Stritzker et al. |
| 7,790,860 B2 | 9/2010 | Thorpe et al. |
| 7,824,708 B2 | 11/2010 | Leverett et al. |
| 8,231,895 B2 | 7/2012 | de Almeida Moreira et al. |
| 8,404,271 B2 | 3/2013 | Byrne |
| 8,450,460 B2 | 5/2013 | Hill et al. |
| 8,461,311 B2 | 6/2013 | Hawkins et al. |
| 8,492,081 B2 | 7/2013 | Nichols et al. |
| 8,512,718 B2 | 8/2013 | Eini et al. |
| 8,518,376 B2 | 8/2013 | Tamarkin et al. |
| 8,524,681 B2 | 9/2013 | Puri et al. |
| 8,545,869 B2 | 10/2013 | Li et al. |
| 8,546,088 B2 | 10/2013 | Lindsey |
| 2013/0034599 A1 | 2/2013 | Thaxton et al. |

FOREIGN PATENT DOCUMENTS

| | | |
|---|---|---|
| WO | WO 92/22331 A1 | 12/1992 |
| WO | WO 02/078672 A2 | 10/2002 |

OTHER PUBLICATIONS

Mo et al. "ATP-triggered anticancer drug delivery", *Nature Communications* 5(3364):1-10 (2014).
Mudshinge et al. "Nanoparticles: Emerging carriers for drug delivery", *Saudi Pharmaceutical Journal* 19:129-141 (2011).
Naito et al. "A Phenylboronate-Funcationalized Polyion Complex Micelle for ATP-Triggered Release of siRNA", *Angew. Chem. Int. Ed.* 51:10751-10755 (2012).
Notification of Transmittal of the International Search Report and the Written Opinion of the International Searching Authority, or the Declaration corresponding to International Application No. PCT/US2014/061334 dated Feb. 5, 2015.
Notification Concerning Transmittal of International Preliminary Report on Patentability corresponding to International Application No. PCT/US2014/061334 dated May 6, 2016.

*Primary Examiner* — Sean McGarry
(74) *Attorney, Agent, or Firm* — Myers Bigel, P.A.

(57) ABSTRACT

A construct for selectively delivering a compound of interest to a cell, includes (a) a bioresorbable polymer shell; (b) a nucleic acid duplex contained in said shell, the duplex comprising (i) an ATP binding nucleic acid, and (ii) a complementary nucleic acid hybridized to the ATP binding nucleic acid; (c) a compound of interest intercalated in or caged by the nucleic acid duplex; (d) optionally, but in some embodiments preferably, a cationic polymer in said polysaccharide shell; and (e) optionally, but in some embodiments preferably, a cell targeting ligand coupled to the polymer shell. The polymer shell is degraded in a cell of interest, or in the extracellular matrix of a tissue carrying said cell of interest, to release said duplex therein. The wherein said duplex is destabilized by binding of ATP in the cell of interest to release the compound of interest therein.

17 Claims, 21 Drawing Sheets

SEQUENCE LISTING

```
<160> NUMBER OF SEQ ID NOS: 5

<210> SEQ ID NO 1
<211> LENGTH: 27
<212> TYPE: DNA
<213> ORGANISM: Artificial
<220> FEATURE:
<223> OTHER INFORMATION: Synthetic ATP aptamer sequence

<400> SEQUENCE: 1
acctggggga gtattgcgga ggaaggt                                        27

<210> SEQ ID NO 2
<211> LENGTH: 27
<212> TYPE: DNA
<213> ORGANISM: Artificial
<220> FEATURE:
<223> OTHER INFORMATION: Synthetic cDNA of ATP aptamer sequence

<400> SEQUENCE: 2
accttcctcc gcaatactcc cccaggt                                        27

<210> SEQ ID NO 3
<211> LENGTH: 27
<212> TYPE: DNA
<213> ORGANISM: Artificial
<220> FEATURE:
<223> OTHER INFORMATION: Synthetic Cy5.5-labeled cDNA sequence
<220> FEATURE:
<221> NAME/KEY: misc_feature
<222> LOCATION: (1)..(1)
<223> OTHER INFORMATION: Cy-5.5 label

<400> SEQUENCE: 3
accttcctcc gcaatactcc cccaggt                                        27

<210> SEQ ID NO 4
<211> LENGTH: 27
<212> TYPE: DNA
<213> ORGANISM: Artificial
<220> FEATURE:
<223> OTHER INFORMATION: Synthetic control aptamer sequence

<400> SEQUENCE: 4
acctggggga gtattgtaaa aaagaat                                        27

<210> SEQ ID NO 5
<211> LENGTH: 27
<212> TYPE: DNA
<213> ORGANISM: Artificial
<220> FEATURE:
```

-continued

```
<223> OTHER INFORMATION: Synthetic cDNA of control aptamer sequence

<400> SEQUENCE: 5
attctttttt acaatactcc cccaggt                                          27
```

METHODS AND CONSTRUCTS FOR COMPOUND DELIVERY

STATEMENT OF PRIORITY

This application is a 35 U.S.C. § 371 national phase application of PCT Application PCT/US2014/061334, filed Oct. 20, 2014 which claims the benefit of U.S. Provisional Application Ser. No. 61/893,450, filed Oct. 21, 2013, the entire contents of each of which are incorporated by reference herein.

STATEMENT REGARDING ELECTRONIC FILING OF A SEQUENCE LISTING

A Sequence Listing in ASCII text format, submitted under 37 C.F.R. §1.821, entitled 5051-843 ST25.txt, 1,417 bytes in size, generated on Apr. 11, 2016 and filed via EFS-Web, is provided in lieu of a paper copy. The Sequence Listing is incorporated herein by reference into the specification for its disclosures.

FIELD OF THE INVENTION

The present invention concerns constructs such as nanodepots for delivering active compounds such as detectable compounds or cytotoxic compounds to cells, compositions containing the same, and methods of use thereof.

BACKGROUND OF THE INVENTION

Nanocarrier-based drug delivery systems (DDSs) offer new opportunities to improve bioactivity and prolong bioavailability of drugs for cancer therapy[1-4]. To further enhance biological specificity and therapeutic efficacy, significant efforts have been devoted to explore active targeting[5] and stimuli responsive DDSs[6], which specifically accumulate at the tumor site and are stimulated to release drugs within tumor cells. These stimuli can be a variety of external signals, such as temperature[7], light[8], magnetic field[9], ultrasound[10] and electric current[11] as well as physiological factors, such as pH[12], redox potential[13], enzymatic activities[14] and glucose levels[15, 16]. A number of nanosystems including liposomes[17], polymeric nanoparticles[18] and inorganic particles[19] have been developed to apply these triggering cues to tailor pharmacokinetics and enhance delivery efficiency. For example, acid-sensitive species have been widely incorporated in intracellular delivery vehicles that undergo an endocytosis pathway, thereby allowing drugs to be readily released in acidic compartments[12]. The gradient of reduced glutathione (GSH) enables polymeric nanogels crosslinked with GSH-cleavable disulfides to efficiently release payloads inside cells[20]. The proteases highly expressed in specific tumor microenvironments facilitate nanocarriers consisting of relevant peptidyl substrates to release drugs on demand[14].

SUMMARY OF THE INVENTION

A first aspect of the invention is a construct for selectively delivering a compound of interest to a cell, comprising:
  (a) optionally but preferably a bioresorbable polymer shell;
  (b) a nucleic acid duplex contained in said shell, said duplex comprising (i) an ATP binding nucleic acid, and (ii) a complementary nucleic acid hybridized to said ATP binding nucleic acid;
  (c) a compound of interest intercalated in or caged by said nucleic acid duplex;
  (d) optionally, but in some embodiments preferably, a cationic polymer in said polysaccharide shell; and
  (e) optionally, but in some embodiments preferably, a cell targeting ligand coupled to said polymer shell;

wherein said polymer shell is degraded in a cell of interest, or in the extracellular matrix of a tissue carrying said cell of interest, to release said duplex therein; and wherein said duplex is destabilized by binding of ATP in said cell of interest to release said compound of interest therein.

A second aspect of the invention is a construct for delivering first and second compounds of interest to a cell, comprising:
  (a) a cross-linked polymer shell;
  (b) a liposome contained in said polysaccharide shell, said liposome comprising a core and a lipid membrane surrounding said core; (c) a first compound of interest (e.g., doxorubicin) contained in said liposome core; and
  (d) a second compound of interest (e.g., TNF-related apoptosis-inducing ligand, or "TRAIL") contained in said polysaccharide shell, and separated from said first compound of interest by said liposome membrane;
  (e) optionally, but in some embodiments preferably, a cell-targeting ligand coupled to said polysaccharide shell.

A further aspect of the invention is a composition comprising a construct as described herein in a pharmaceutically acceptable carrier.

A further aspect of the invention is a method of delivering a compound of interest, or a first and second compound of interest to a cell, comprising the steps of: (a) providing a construct as described above, and then (b) contacting said construct to said cell, or a tissue carrying said cell, under conditions in which said compound(s) of interest is/are released therefrom.

A further aspect of the invention is a method of treating cancer in a subject in need thereof, comprising administering said subject a construct as described herein in a treatment effective amount, wherein said first, and second compounds of interest each comprises an anticancer or antineoplastic agent.

Yet a further aspect of the invention is the use of a construct described herein for the treatment of cancer or for the preparation of a medicament for the treatment of cancer.

The present invention is explained in greater detail below. The disclosures of all United States patents cited herein are to be incorporated herein by reference.

DETAILED DESCRIPTION OF ILLUSTRATIVE EMBODIMENTS

Figure 1:
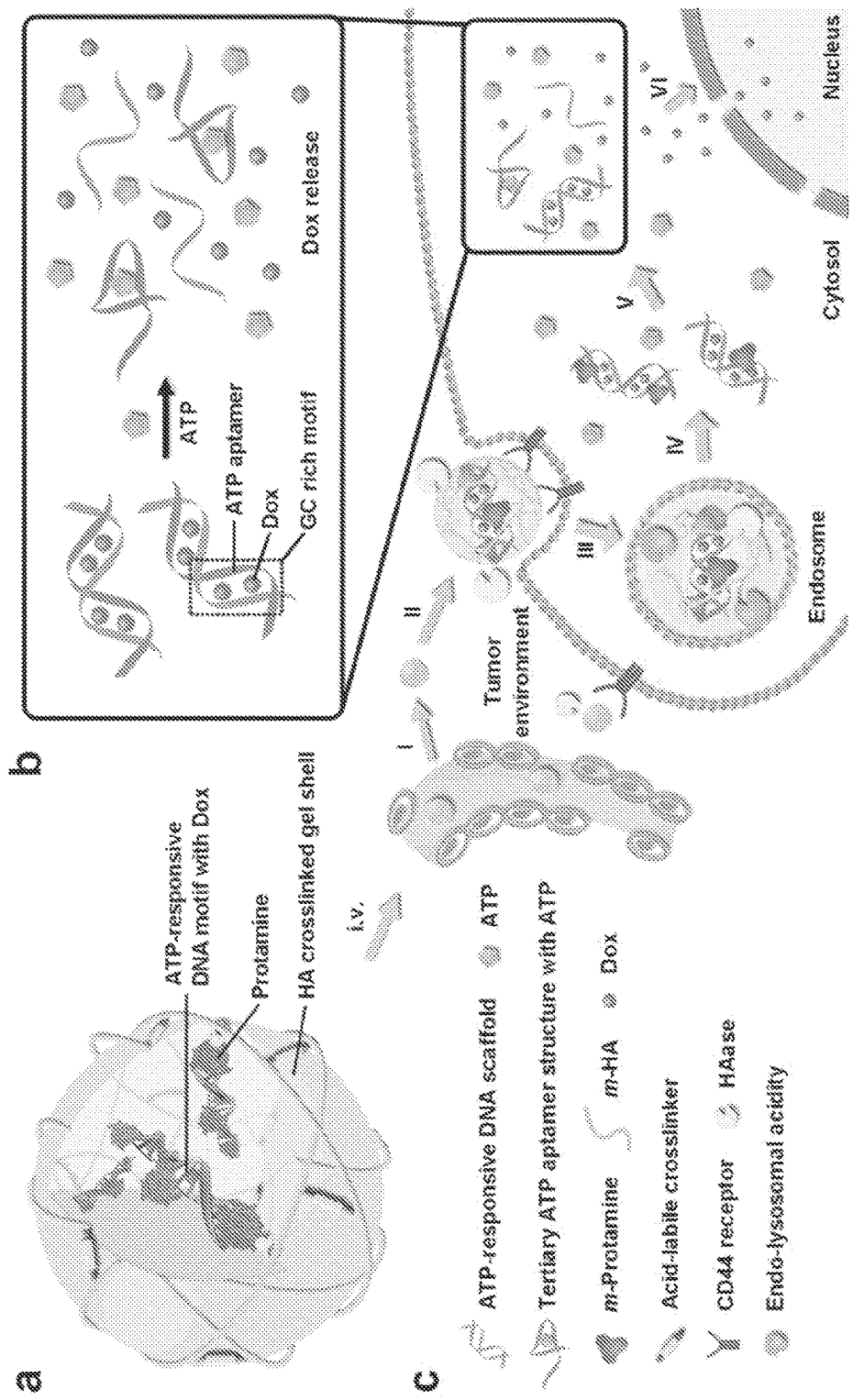
FIG. 1. Schematic design of the ATP-triggered Dox release system. (a) The main components of Dox/NG: ATP-responsive DNA motif with Dox, protamine and a HA crosslinked gel shell. (b) Mechanism of ATP-triggered release of Dox based on the structural change of duplex-to-aptamer. (c) ATP-responsive delivery of Dox by Dox/NG to nuclei for the targeted cancer therapy. I, accumulation of Dox/NG at the tumor site through passive and active targeting; II, specific binding to the overexpressing receptors on the tumor cells and degradation of HA shell by HAase rich in the tumor extracellular matrix; III, receptor-mediated endocytosis; IV, endosomal/lysosomal escape; V, ATP-triggered Dox release in the cyotosol; VI, accumulation of Dox in the nucleus.

"Compound of interest" may be any suitable compound, including detectable compounds, cytotoxic compounds, antiviral compounds, etc., non-limiting examples of which are discussed further below.

"First compound of interest" and "second compound of interest" as used herein are typically two different compounds, e.g., a detectable compound in combination with either a cytotoxic or antiviral compound; a pair of different but complementary cytotoxic compounds; a pair of different but complementary antiviral compounds; etc.

"Detectable compound" as used herein may be any suitable detectable compound, such as a fluorescent dyes, a magnetic or paramagnetic particle or nanoparticle, a radiolabelled compound, etc. Examples include but are not limited to those described in U.S. Pat. Nos. 8,546,088; 8,492,081; 7,790,860; 7,763,420; etc. In some embodiments the detectable compound may be conjugated to or covalently coupled to an intercalating agent as discussed below.

"Antiviral compound" may be any suitable agent, including those that interfere with viral synthesis or propagation after cell entry such as reverse transcriptase inhibitors and viral polymerase inhibitors. Numerous examples are known, including but not limited to those described in U.S. Pat. Nos. 8,518,376; 8,512,718; 8,404,271; etc.

"Cytotoxic compound" may be any suitable cytotoxic agent, including antibiotic and chemotherapeutic agents (i.e., antineoplastic or anticancer agents). Examples include but are not limited to those described in U.S. Pat. Nos. 8,231,895; 7,588,778; 6,404,710; 5,804,568; etc. In some embodiments the cytotoxic compound is itself an intercalating agent, as described below, or is conjugated to or covalently coupled to an intercalating agent, as discussed below. In some embodiments the cytotoxic compound may be a tumor necrosis factor superfamily cytokine domain, as discussed further below.

"Tumor necrosis factor (TNF) superfamily cytokine domains" as used herein are known. Examples include, but are not limited to, CD95 ligands TNF-related apoptosis-inducing ligands (TRAIL), and soluble forms thereof. See, e.g., U.S. Pat. Nos. 8,461,311; 8,450,460.

"Intercalating agent" as used herein may be any compound that binds to a nucleic acid duplex, but not to either strand thereof when in single-stranded form. Examples of intercalating agents include, but are not limited to, doxorubicin, daunorubicin, epirubicin, idarubicin, valrubicine, mitoxantrone, etc. The anthracycline antibiotics are a known group of intercalating agents. Note that additional compounds or groups can be covalently coupled to an intercalating agent through a suitable linking group in accordance with known techniques (see, e.g., U.S. Pat. No. 5,122,368) to provide a broad variety of compounds with diverse activities that intercalate into a nucleic acid duplex.

"Bioresorbable polymer" as used herein may be any suitable polymer, in some embodiments a cross-linked polymer. Examples of suitable polymers include, but are not limited to, crosslinked polymers or copolymers of a polyacrylic acid, polymethacrylic acid, polyethylene amine, a polysaccharide, alginic acid, a pectinic acid, carboxy methyl cellulose, hyaluronic acid, heparin, chitosan, carboxymethyl chitosan, carboxymethyl starch, carboxymethyl dextran, heparin sulfate, chondroitin sulfate, cationic starch, or salts thereof. See, e.g., U.S. Pat. No. 8,545,869.

"Cationic polymer" as used herein may be any suitable charged polymer, preferably a carrier carrying multiple charges. Such a polymer may be a protein, peptide, etc. Examples include, but are not limited to, protamine, cell penetrating peptide (CPP), polyarginine, polyhistidine, polylysine, or a combination thereof.

"Cell targeting ligand" as used herein may be any cell-directing molecule that has specificity for targeted sites such as cell surface receptors. "Specificity for targeted sites" means that upon contacting the cell targeting ligand with a cell, under physiological conditions of ionic strength, temperature, pH and the like, specific binding will occur. The cell-ligand interaction may occur due to specific electrostatic, hydrophobic, or other interaction of certain residues of the ligand with specific residues of the cell to form a stable complex under conditions effective to promote the interaction. Examples of cell targeting ligands include, but are not limited to, polynucleotides, oligonucleotides, polyamides, peptides having affinity for a cellular receptor, proteins such as antibodies, fatty acids, vitamins, flavonoids, sugars, antigens, receptors, reporter molecules, reporter enzymes, chelators, porphyrins, intercalators, steroids and steroid derivatives, hormones such as progestins (e.g. progesterone), glucocorticoids (e.g., cortisol), mineralocorticoids (e.g., aldosterone), androgens (e.g., testosterone) and estrogens (e.g., estradiol), histamine, hormone mimics such as morphine, and macrocycles. A peptide having affinity for a cellular receptor may include an endorphin, an enkephalin, a growth factor, e.g. epidermal growth factor, poly-L-lysine, a hormone, insulin, ribonuclease, serum albumin binding peptide, a peptide region of a protein and other molecules that are capable of penetrating cellular membranes, either by active transport or passive transport. See, e.g., U.S. Pat. No. 8,524,681; see also M. Barry et al., *Toward cell-targeting gene therapy vectors: Selection of cell-binding peptides from random peptide presenting phage libraries*, Nature Medicine 2, 299-305 (1996).

"Liposome" as used herein may be any suitable liposome. Numerous liposome constructs are known. In general, liposomes have a liquid (typically aqueous) core or a solid core (see, e.g., U.S. Pat. No. 4,839,111 to Huang), which core is surrounded by a lipid membrane. The lipid membrane. The lipid membrane may be a bilayer, or multiple layers, as in unilamellar and multilamellar liposomes. Examples include but are not limited to those liposomes described in U.S. Pat. Nos. 7,824,708; 7,465,753; 7,390,780; 7,386,691; 7,244,449; 4,356,167; 3,932,657; etc.

"Treat" as used herein refers to any type of treatment that imparts a benefit to a patient, particularly delaying or retarding the progression disease.

"Pharmaceutically acceptable" as used herein means that the compound or composition is suitable for administration to a subject to achieve the treatments described herein, without unduly deleterious side effects in light of the severity of the disease and necessity of the treatment.

Constructs.

ATP-targeted constructs. As noted above, the present invention provides, in some embodiments, a construct for selectively delivering a compound of interest to a cell, comprising: (a) optionally but preferably a bioresorbable polymer shell; (b) a nucleic acid duplex contained in said shell, said duplex comprising (i) an ATP binding nucleic acid, and (ii) a complementary nucleic acid hybridized to said ATP binding nucleic acid; (c) a compound of interest intercalated in or caged by said nucleic acid duplex; (d) optionally, but in some embodiments preferably, a cationic polymer in said polysaccharide shell; and (e) optionally, but in some embodiments preferably, a cell targeting ligand coupled to said polymer shell; wherein said polymer shell is degraded in a cell of interest, or in the extracellular matrix of a tissue carrying said cell of interest, to release said duplex therein; and wherein said duplex is destabilized by binding of ATP in said cell of interest to release said compound of interest therein.

In some embodiments of the foregoing, the bioresorbable polymer shell has an average diameter of from 1 or 10 nanometers to 500 or 1000 nanometers.

In some embodiments of the foregoing, the ATP binding nucleic acid comprises an ATP binding aptamer.

In some embodiments of the foregoing, the complementary nucleic acid comprises DNA.

In some embodiments of the foregoing, the compound of interest is a detectable compound or a cytotoxic compound.

In some embodiments of the foregoing, the compound of interest comprises a DNA intercalating agent (e.g., doxorubicin, daunorubicin, epirubicin, idarubicin, valrubicine, mitoxantrone, or a combination thereof).

Dual Compound Delivery Constructs.

As also noted above, the present invention, second aspect of the invention is a construct for delivering first and second compounds of interest to a cell, comprising: (a) a crosslinked polymer shell; (b) a liposome contained in said polysaccharide shell, said liposome comprising a core and a lipid membrane surrounding said core; (c) a first compound of interest contained in said liposome core; and (d) a second compound of interest contained in said polysaccharide shell, and separated from said first compound of interest by said liposome membrane; and (e) optionally, but in some embodiments preferably, a cell-targeting ligand coupled to said polysaccharide shell.

In some embodiments of the foregoing, the bioresorbable polymer shell has an average diameter of from 1 or 10 nanometers to 500 or 1000 nanometers.

In some embodiments of the foregoing, the liposome core comprises an aqueous core.

In some embodiments of the foregoing, the first compound of interest is a detectable compound or a cytotoxic compound.

In some embodiments of the foregoing, the first compound of interest comprises a DNA intercalating agent (e.g., doxorubicin, daunorubicin, epirubicin, idarubicin, valrubicine, mitoxantrone, or a combination thereof).

In some embodiments of the foregoing, the second compound of interest comprises a tumor necrosis factor (TNF) superfamily cytokine domain such as TRAIL.

Methods of Use

As noted above, the present invention provides methods of delivering a compound, or a pair of compounds, of interest to a cell, comprising the steps of: (a) providing a construct as described above; and then (b) contacting the construct to the cell or a tissue carrying said cell, under conditions in which said compound of interest is released therefrom. The cells may be in vitro, such as in a cell culture or fermentation process, or the cells may be in vivo, such as in a tissue culture or in an animal subject.

The method may be used to deliver compounds of interest for any reason, such as detecting cells, killing cells (e.g., a targeted cell type in a culture media), treating a disorder or condition (e.g., cancer, a viral infection or phage infection in vivo or in vitro), etc.

The cells or tissues may be of any type, including plant and animal cells, and prokaryotic or eukaryotic cells, depending on the particular use. Animal cells or tissues may be of any suitable type, including mammalian, avian, reptile, amphibian, etc.

Where compounds are administered to cells in vivo, the present invention is primarily concerned with the treatment of human subjects, but the invention may also be carried out on animal subjects, particularly mammalian subjects such as dogs, cats, livestock and horses for veterinary purposes. While subjects may be of any suitable age, the subjects are in some embodiments neonatal, infant, juvenile, adolescent, adult, or geriatric subjects.

In some embodiments, the invention provides a method of treating cancer in a subject in need thereof, comprising administering the subject a construct as described above in a treatment effective amount, wherein the compound or compounds of of interest comprises an anticancer or antineoplastic agent. Illustrative cancers that may be treated (depending upon the particular choice of compounds administered) include but are not limited to lung, skin, prostate, breast, ovarian, endometrial, colorectal, pancreatic, kidney, bladder, liver, and brain cancer, or leukemia or lymphoma.

Pharmaceutical Formulations.

The active compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound(s), which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use.

Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any specific active compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. Typically, a dosage from about 0.5 mg/kg to 5 mg/kg may be employed for intramuscular injection.

The present invention is explained in greater detail in the following non-limiting examples.

EXAMPLE 1

ATP-Triggered Anticancer Drug Delivery

Stimuli-triggered drug delivery systems (DDSs) have been increasingly used to promote physiological specificity and on-demand therapeutic efficacy of anticancer drugs. Here we utilized adenosine-5'-triphosphate (ATP), the major energy currency of cells, as a novel trigger for the controlled release of anticancer drugs. We demonstrate that polymeric nanocarriers functionalized with an ATP-binding aptamer incorporated DNA motif can selectively release the intercalating doxorubicin (Dox) via a conformational switch when in an ATP rich environment. The targeted in vitro cytotoxicity and apoptotic activity of Dox was significantly enhanced by the intracellular ATP-triggered drug release. Equipped with an outer shell crosslinked by hyaluronic acid, a specific tumor-targeting ligand, the ATP-responsive nanocarriers presented remarkable improvement in the chemotherapeutic inhibition of tumor growth using xenograft MDA-MB-231 tumor-bearing mice. This ATP-triggered drug release system opens the door for the exploration of more sophisticated DDSs, which can associate with the tumor metabolism and differentiate ATP levels to facilitate the selective release of drug cargos.

We here report for the first time, adenosine-5'-triphosphate (ATP), the most abundant ribonucleotide used in cells as a coenzyme, can serve as a new trigger for the controlled release of anticancer drugs both in vitro and in vivo. As the "molecular unit of currency" of intracellular energy transfer, ATP transports chemical energy within cells to support metabolism[21]. ATP is present in low concentrations (<0.4 mM) in the extracellular environment, but is relatively concentrated within the intracellular cytosol (1-10 mM)[22-25]. Within cells, ATP provides energy to the cellular metabolism by breaking a phosphoanhydride bond. The prominent difference in the ATP level between the extracellular and intracellular environments is the biological rationale for design of ATP-mediated drug release systems, which remain elusive to date[26, 27]. We envision that ATP-responsive nanosystems can be functionalized with ATP-binding aptamers, which are specifically recognized and activated by ATP and subsequently promote the release of preloaded anticancer drugs.

To this end, we designed an all-biopolymer nanocarrier comprised of DNA, protein, and polysaccharide. As shown in FIG. 1a, the final formulation (designated nanogel) is mainly comprised of three distinct functional constituents: 1) an ATP-responsive DNA motif with doxorubicin (Dox), 2) protamine and 3) a hyaluronic acid (HA) crosslink shell. The DNA scaffold consists of the ATP aptamer and its complementary single stranded DNA (cDNA), the structure of which has been previously used to detect ATP[28-31]. The GC pairs of the DNA motif provides faithful loading sites for Dox, a model chemotherapeutic drug used to treat a wide spectrum of cancers, including breast cancer, ovarian cancer, and acute leukemia. In the presence of ATP, the tertiary structure of the ATP aptamer is stabilized, which causes the DNA duplex to dissociate and thereby liberates cDNA. In our strategy, this structural change from the duplex to the tertiary aptamer structure (duplex-to-aptamer) results in the intercalated Dox to be released from the duplex (FIG. 1b). Protamine is positively charged, and is applied to compress the negatively charged DNA scaffold into a cationic core complex, which has enhanced cell penetration, endosomal escape and nuclear targeting effects[32]. Anionic HA is coated on the core complex to form a protective shell, and also supports active tumor targeting ligands to bind the receptors, such as CD44 and RHAMM, which are overexpressd on the cell surface of several tumors[33]. Additionally, hyaluronidases (HAase)[34], rich in various malignant tumor matrices and the tumor cellular endocytic vesicles including endosomes and lysosomes (endo-lysosomes)[35], leads to the degradation of the HA shell and allows the exposure of the cationic complex to facilitate intracellular delivery. To obtain the compact "gel" structure[36], both protamine and HA are modified with acrylamide (designated m-Protamine) and acrylate groups (designated m-HA), respectively. The final nanogels are constructed by photocrosslinking via UV irradiation.

After intravenous injection, the nanogel is expected to accumulate at tumor sites as a result of passive and active targeting effects. HAase degrades the HA shell, thereby exposing the complex of protamine and the Dox-intercalated duplex (Dox/Duplex). The protamine component promotes endosomal escape of the complex, allowing the efficient transport of Dox/Duplex into the cytosol. Dox/Duplex dissociates at the significantly higher ATP in the cytosol compared with the extracellular fluid, thereby yielding the release of intercalating Dox, which eventually accumulates in the nuclei to produce cytotoxicity and apoptosis (FIG. 1c). This ATP-triggered drug release system offers new avenues for exploration of more sophisticated DDSs, which integrates with tumor metabolism for highly selective controlled release of anticancer drugs.

Results

Figure 2:
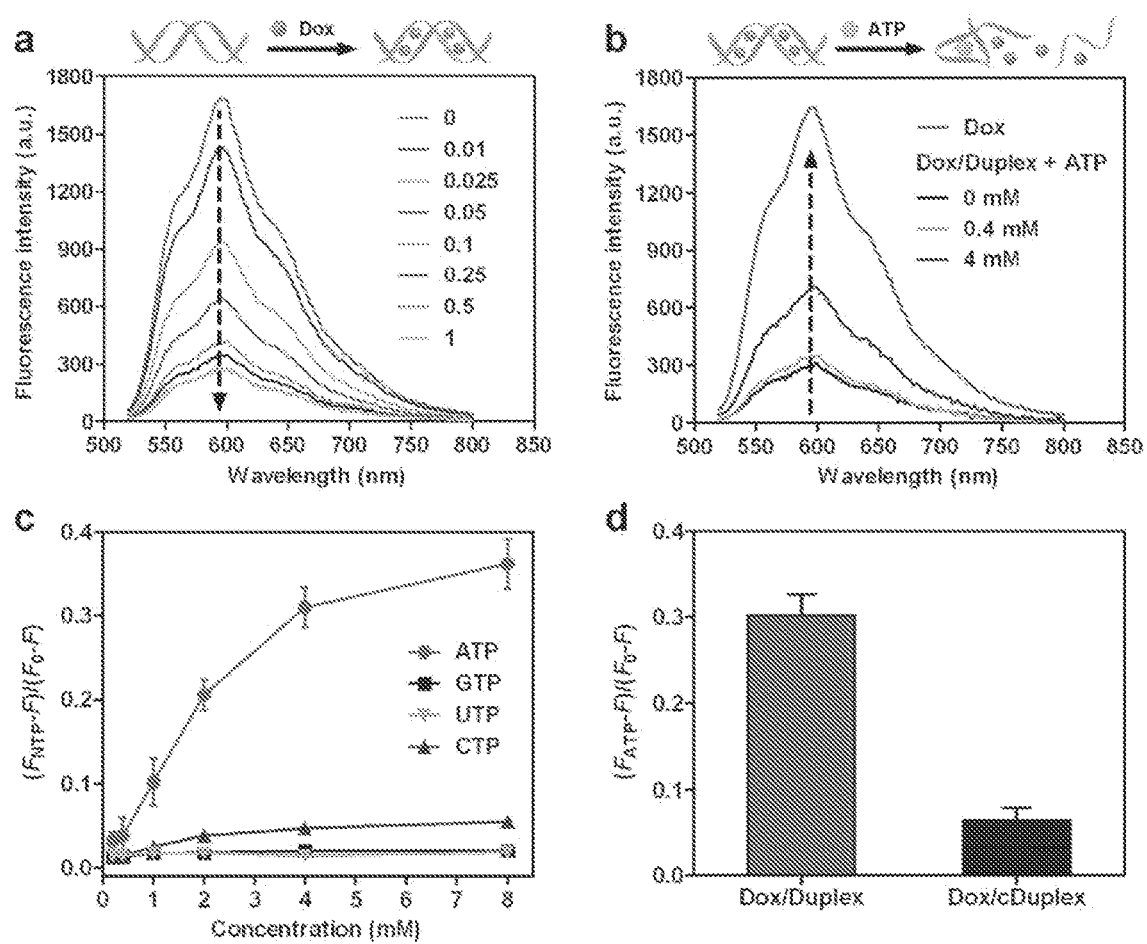
FIG. 2. ATP-triggered Dox release from duplex. (a) The fluorescence spectra of the Dox solution (1.33 µM) with increasing molar ratios of hybridized DNA duplex of ATP aptamer and its complementary single stranded DNA (from top to bottom: 0, 0.01, 0.025, 0.05, 0.1, 0.25, 0.5, 1 equiv.). (b) The fluorescence spectra of Dox/Duplex (1.33 μM) at the molar ratio of Dox to duplex as 2:1 in the presence of different concentrations of ATP (0, 0.4, 4 mM). (c) Fluorescence recovery ratio of Dox/NG in the presence of different concentrations of ATP, GTP, CTP and UTP (0.2, 0.4, 1, 2, 4, 8 mM). (d) Fluorescence recovery ratio of Dox/NG and Dox/cNG in the presence of 4 mM ATP.
Figure 6:
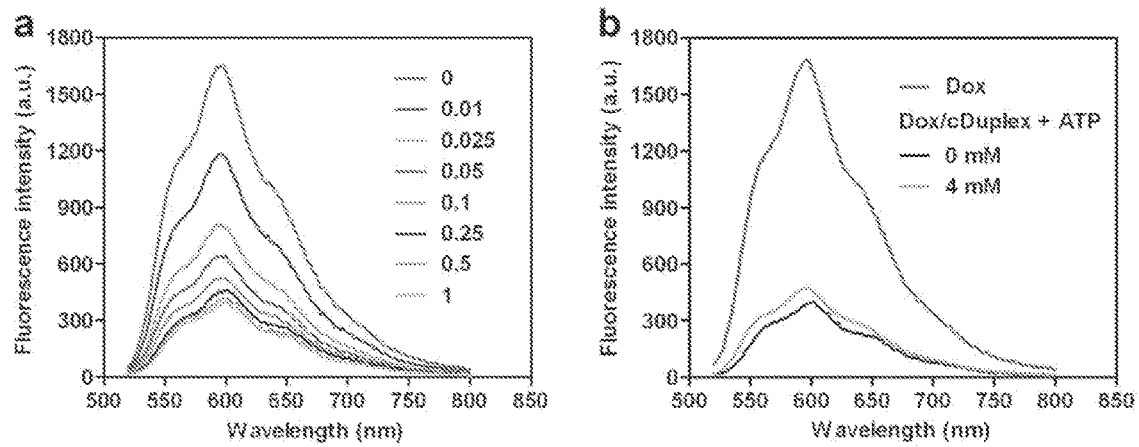
FIG. 6. (a) The fluorescence spectra of the Dox solution (1.33 μM) with the increasing molar ratios of hybridized cDNA duplex of the control aptamer and its cDNA (from top to bottom: 0, 0.01, 0.025, 0.05, 0.1, 0.25, 0.5, 1 equiv.). (b) The fluorescence spectra of Dox/cDuplex (1.33 μM) in the absence and presence of a 4 mM ATP concentration.

ATP-triggered Dox release from duplex. We first designed a DNA scaffold by hybridizing an ATP aptamer and its cDNA (Table 1), which has a 27-base pair with GC rich motif for anthracycline-contained Dox loading[37]. To evaluate the amount of Dox molecules loaded into the ATP-Duplex, we measured Dox intercalation by monitoring Dox fluorescence intensity changes. As shown in FIG. 2a, when a fixed concentration of Dox was incubated with an increasing molar ratio of the DNA duplex, a sequential decrease was found in the fluorescence intensity of Dox due to the initiation of forster resonance energy transfer (FRET) between Dox molecules when intercalated into the DNA duplex[38, 39]. A maximum quenching efficacy was achieved when the molar ratio of Dox to duplex was 2:1. To investigate the ATP-responsive characteristics of the duplex, Dox/Duplex was incubated at 0.4 mM and 4 mM ATP concentrations, which represent the typical ATP level in the extracellular fluid and intracellular cytosol, respectively[22-25]. The dissociation of Dox/Duplex leads to the release of Dox, which can be estimated by detecting the recovery of the Dox fluorescence. As shown in FIG. 2b, a remarkable fluorescence recovery was observed in the presence of 4 mM ATP concentration compared with the 0.4 mM sample, indicating that Dox/Duplex is responsive to high concentrations of ATP. The fluorescence recovery ratio (($F_{NTP}$–F)/($F_0$–F)) showed that Dox release from Dox/Duplex was ATP concentration-dependent (FIG. 2c), where $F_0$ is the fluorescence intensity of Dox in the Dox solution without the duplex, and $F_{NTP}$ and F are the fluorescence intensities of Dox in Dox/Duplex at the same Dox concentration as the Dox solution in the presence and absence of ATP, respectively. The fluorescence recovery ratio was determined as 20% and 31% at ATP concentrations of 2 mM and 4 mM, about 4-fold and 7-fold greater than that at an ATP concentration of 0.4 mM, respectively. In contrast, negligible changes were found in the fluorescence recovery ratio of Dox/Duplex after incubation with the analogues of ATP, such as cytidine triphosphate (CTP), guanosine triphosphate (GTP), and uridine triphosphate (UTP), suggesting that the ATP aptamer-functionalized Dox/Duplex had a good selectivity to ATP compared to its analogues, which were unable to release Dox even at high levels. Furthermore, we took Dox-loaded control duplex (Dox/cDuplex)[30] that had the same length but was not responsive to ATP as a reference (Table 1 and FIG. 6). As presented in FIG. 2d, the fluorescence recovery ratio of Dox/Duplex was about 5-fold of that of Dox/cDuplex in the presence of a 4 mM ATP concentration, substantiating that the ATP aptamer endowed Dox/Duplex with the ATP-responsive drug release capability. Taken together, Dox/Duplex, the ATP-responsive DNA motif encapsulating Dox, can be used to effectively release Dox via a duplex-to-aptamer structural change under elevated ATP concentrations, which provides a foundation for the construction of an ATP-responsive DDS.

Preparation and Characterization of ATP-Responsive Nanogels.

Figure 3:
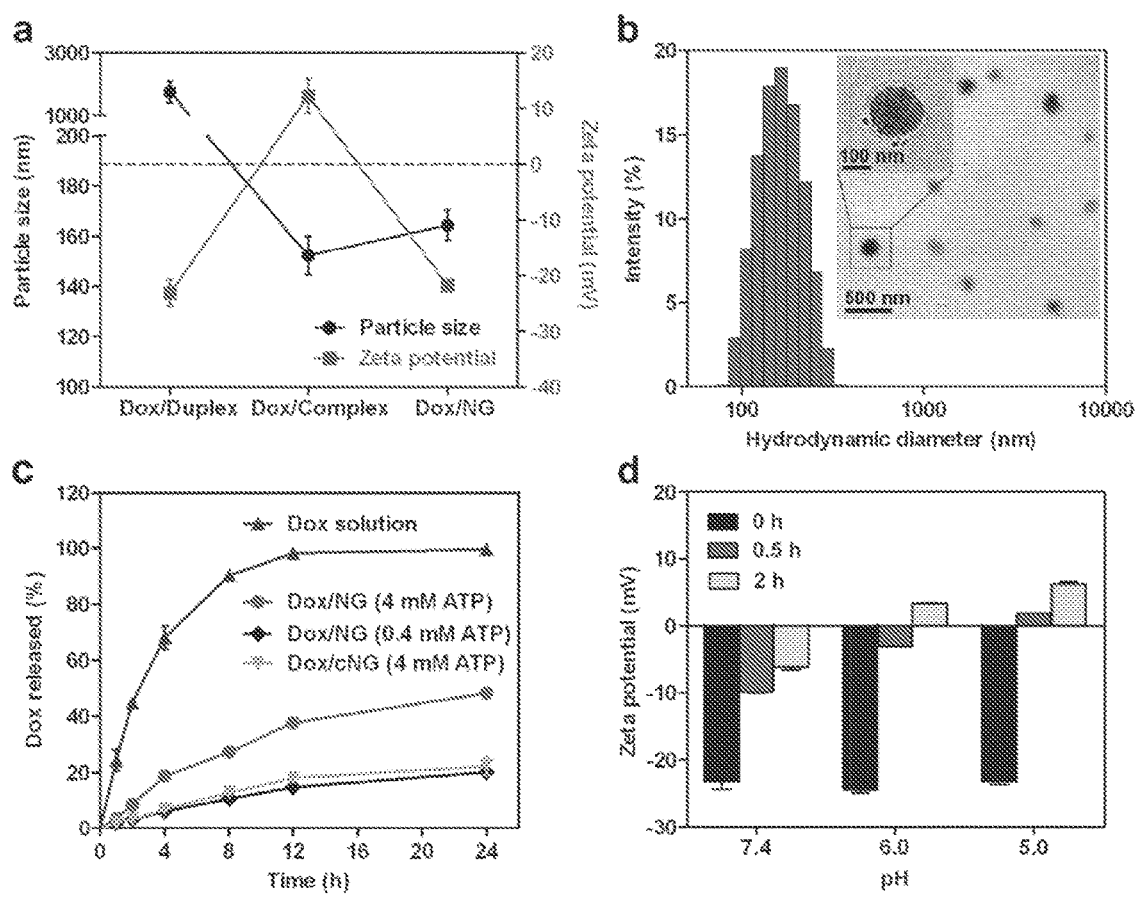
FIG. 3. Characterization of ATP-responsive nanogels. (a) The particle size and zeta potential of Dox/Duplex, Dox/Complex and Dox/NG. (b) The hydrodynamic size of Dox/NG measured by dynamic light scattering (DLS). Inset: TEM image of Dox/NG. (c) In vitro release of Dox/NG and Dox/eNG at different concentrations of ATP. (d) Changes in the zeta potential of Dox/NG incubated with 0.5 mg/mL HAase at different pH values for different time.
Figure 7:
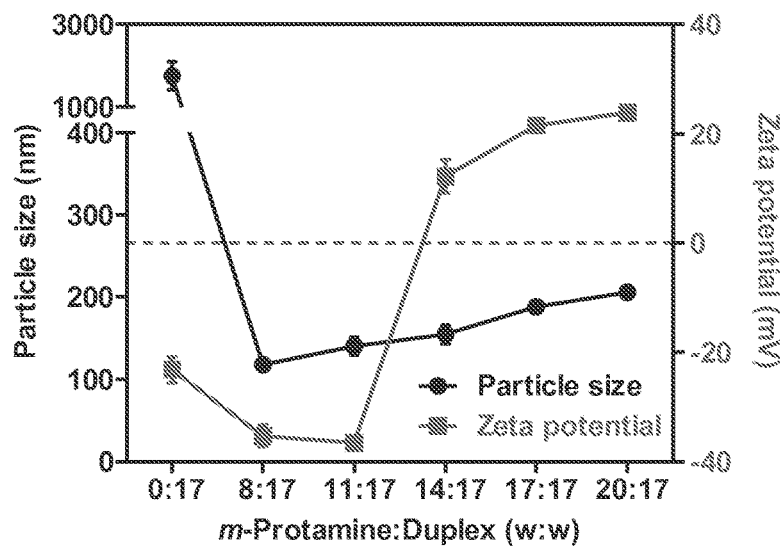
FIG. 7. The particle size and zeta potential of Dox/Complex at different mass ratios of m-Protamine and ATP duplex.
Figure 8:
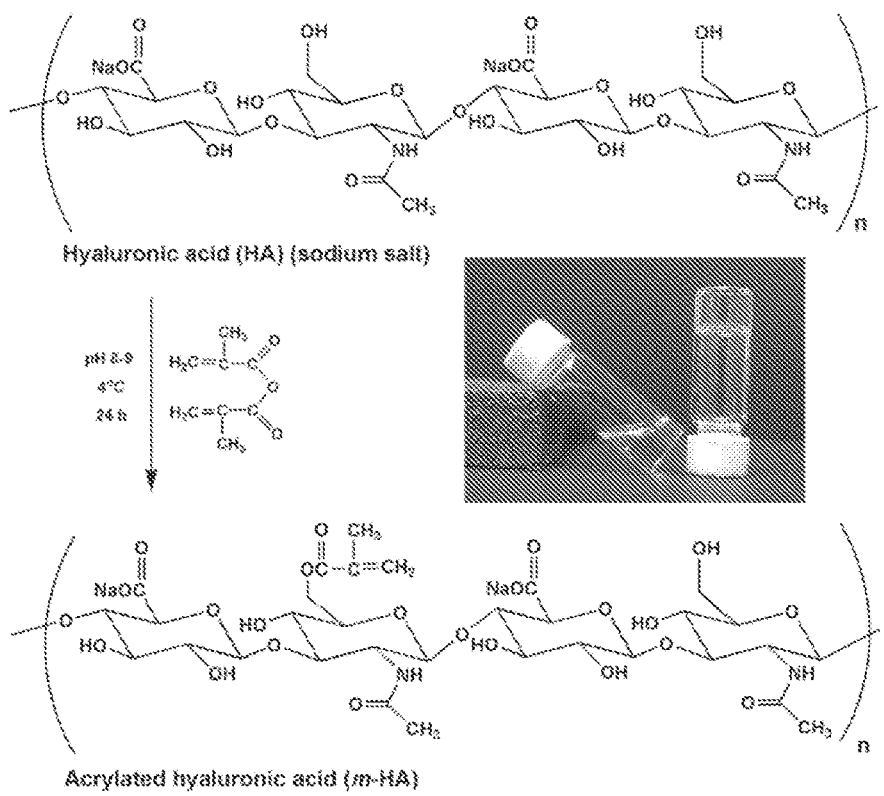
FIG. 8. Synthesis of m-HA. Inset: The hydrogel can be formed by m-HA (2%, w:v) (right) by Irgacure 2959 (0.1%, w:v) via UV irradiation for 30 s in contrast to HA with the same concentration (left).
Figure 9:
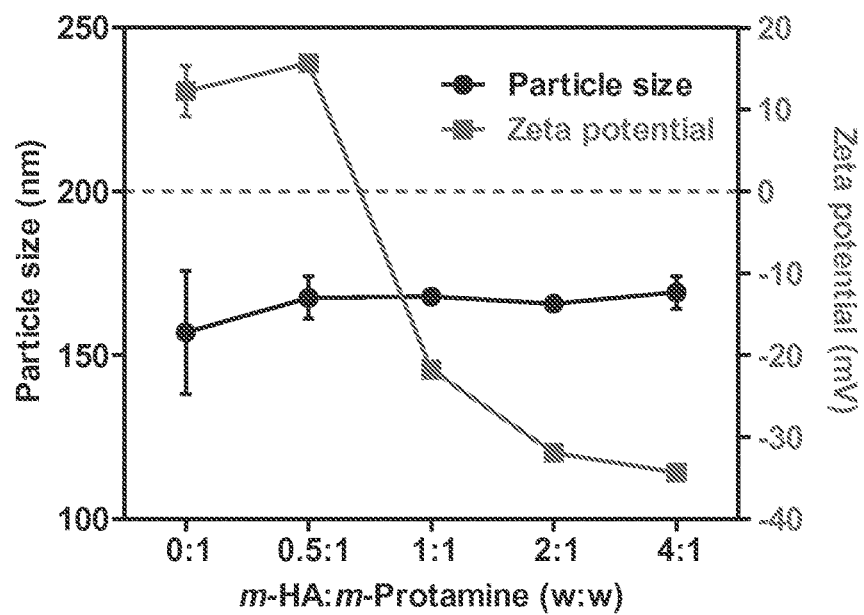
FIG. 9. The particle size and zeta potential of Dox/HA-Complex at different mass ratios of m-HA and m-Protamine.
Figure 10:
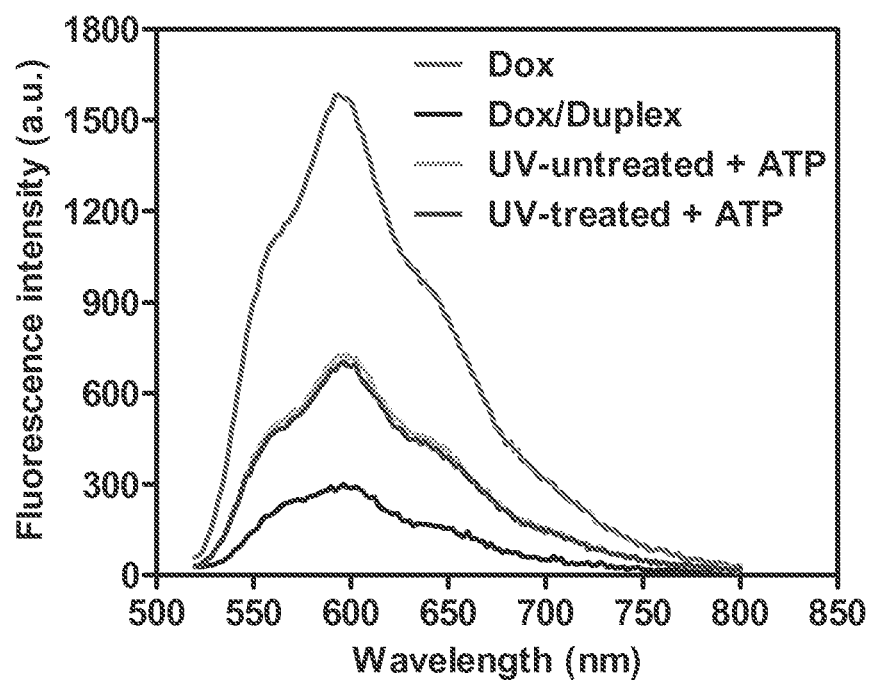
FIG. 10. The fluorescence spectra of Dox/Duplex (1.33 μM) in the presence of 4 mM ATP concentration before and after UV treatment for 60 s.

Dox/Duplex was mixed with m-Protamine at an optimal mass ratio of 14:17 to prepare a positively charged Dox-loaded complex[40] (Dox/Complex) (FIG. 7). The complex was then added to m-HA solution at a mass ratio of m-HA to m-Protamine as 1:1 to obtain a HA coated Dox/Complex (Dox/HA-Complex) with a negative charge (FIG. 8, 9). Ultimately, Dox-loaded nanogel (Dox/NG) was obtained by photocrosslinking Dox/HA-Complex with an acid-labile crosslinker, glycerol dimethacrylate (GDA). Insignificant influence on the ATP-response of Dox/Duplex was found after a short period of UV exposure (FIG. 10). As shown in FIG. 3a, changes in the particle size and zeta potential from Dox/Duplex to Dox/NG suggested an efficient HA coating of the complex and the successful synthesis of Dox/NG, which had a resulting particle diameter of about 160 nm and a zeta potential of −20 mV. Transmission electron microscope (TEM) imaging further confirmed a spheroid structure of Dox/NG with a uniform particle size of about 150 nm (FIG. 3b).

To evaluate ATP-triggered Dox release characteristics, we investigated in vitro release profiles of Dox from Dox/NG in the presence and absence of ATP at 37° C. As shown in FIG. 3c, both Dox/NG and non-ATP-responsive Dox-loaded control nanogel (Dox/eNG), which consisted of the same components with Dox/NG except Dox/eDuplex, presented a sustained Dox release compared to the Dox solution. More importantly, in the presence of 0.4 mM ATP, only 6% of Dox was released from Dox/NG in the first 4 h and approximately 20% was released within 24 h. In the same buffer solution with 4 mM ATP, a level comparable to intracellular ATP levels, the release of Dox was dramatically accelerated. About 20% of Dox was released from Dox/NG in the first 4 h and more than 40% was released within 24 h. It is also noteworthy that the release of Dox from Dox/cNG (without ATP-sensitivity) was slow even in the presence of 4 mM ATP. It is therefore implied that the ATP aptamer is essential for Dox/NG to recognize ATP concentration and allow the fast release of the intercalated Dox molecules in ATP rich environments, and Dox remains entrapped in the inner cores of Dox/NG at low ATP concentrations.

To demonstrate HA degradation by HAase[34], the variation in the zeta potential of Dox/NG was monitored after incubation with HAase at different pH values over time. As shown in FIG. 3d, the zeta potential of Dox/NG changed sharply from negative to neutral after exposure to HAase for 2 h at pH 7.4. Moreover, the HA shell of Dox/NG crosslinked by GDA showed a pH-dependent degradation. Higher acidities had a concomitant enhancement on the degradation of the shell of Dox/NG. At 2 h, the zeta potential of Dox/NG continuously rose to +3 mV at pH 6.0 and +6 mV at pH 5.0, while Dox/NG still presented slightly negative charge of −6 mV at pH 7.4. Accordingly, the crosslinked HA shell of Dox/NG will be preferentially dissociated in the HAase-rich acidic tumor microenvironment and intracellular endo-lysosome to "turn off" the protective function of HA and "turn on" the penetrating activity of the protamine-based complex for efficient intracellular delivery.

Intracellular ATP-Triggered Dox Release of Dox/NG.

Figure 4:
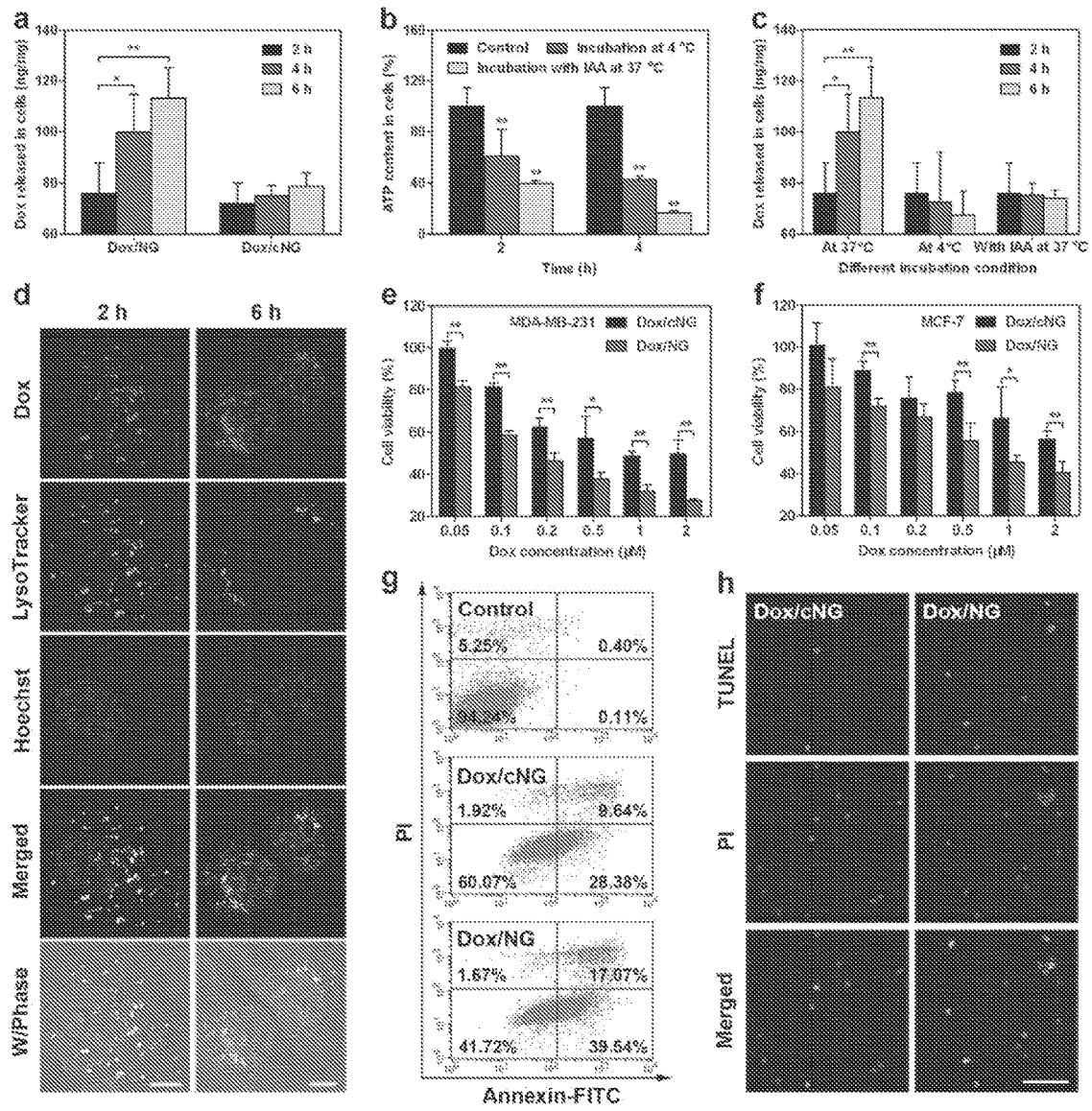
FIG. 4. Intracellular ATP-triggered Dox release. (a) Dox released in MDA-MB-231 cells of Dox/NG and Dox/cNG. The cells were incubated with Dox/NG or Dox/cNG at 37° C. for 2 h, and subsequently incubated with fresh culture medium at 37° C. for additional 2 h or 4 h after removal of the excess nanogels. *P<0.05. P<0.01. (b) The ATP content in MDA-MB-231 cells after different treatments. P<0.01. (c) Dox released in MDA-MB-231 cells of Dox/NG. The cells were incubated with Dox/NG at 37° C. for 2 h, and then incubated with the fresh culture medium at 4° C. or with IAA at 37° C. for additional 2 h or 4 h after removal of the excess nanogels. **P<0.01. (d) Intracellular delivery of Dox/NG on MDA-MB-231 cells at different time observed by CLSM. The cells were incubated with Dox/NG at 37° C. for 2 h, and further incubated with fresh culture medium at 37° C. for additional 4 h after removal of the excess nanogels. The late endosomes and lysosomes were stained by LysoTracker Green, and the nuclei were stained by Hoechst 33342. Scale bars are 10 μm. (e, f) In vitro cytotoxicity of Dox/cNG and Dox/NG on MDA-MB-231 (e) and MCF-7 cells (f) for 24 h. *P<0.05, **P<0.01. (g) Flow cytometric analysis of MDA-MB-231 cell apoptosis induced by Dox/cNG and Dox/NG for 12 h by using Annexin V-FITC/PI staining. (h) MDA-MB-231 cell apoptosis induced by Dox/cNG and Dox/NG for 18 h using the APO-BrdU TUNEL assay. Alexa Fluor 488-stained nick end label showed green fluorescence, and PI-stained nuclei showed red fluorescence. Scale bar is 100 μm.

We next investigated whether intracellular ATP could accelerate the release of Dox determined by the fluorescence recovery of Dox in the cells. To assess this, the human breast adenocarcinoma (MDA-MB-231) cells were incubated with Dox/cNG and Dox/NG for 2 h, respectively, and the excess nanogels were thoroughly removed. The cells were then incubated with fresh culture medium for an additional 2 h or 4 h. The amount of released Dox was evaluated by recording the fluorescence intensity of the whole cells. As shown in FIG. 4a, Dox fluorescence was observed during the first 2 h of the cellular uptake of Dox/NG at 37° C., which resulted from the unquenched background fluorescence of Dox and the Dox released from Dox/NG[39]. Notably, Dox/NG presented a concomitant increase of fluorescence intensity with increasing incubation time of the cells. The fluorescence intensity had 32% and 49% significant increase after an additional 2 h and 4 h of incubation, respectively. However, cells incubated with Dox/eNG showed no evident increase in the Dox fluorescence intensity. This prominent difference in the fluorescence intensity between cells incubated with Dox/NG and Dox/cNG suggested that Dox/NG was able to selectively liberate Dox in a more efficient manner based on the intracellular ATP level by ATP-responsive structural changes, relative to Dox/cNG that released Dox by passive diffusion. To further demonstrate the intracellular ATP concentration-dependent Dox release from Dox/NG, we inhibited the ATP production of the cells by physically lowering the temperature (4° C.) and adding a chemical inhibitor, iodoacetic acid (IAA)[41], and subsequently monitored the fluorescence intensity after the treated cells were incubated with Dox/NG. As shown in FIG. 4b, cell incubation at 4° C. and with IAA at 37° C. both lead to a significant decrease in ATP generation within the cells. As expected, no remarkable release of Dox from Dox/NG was found in the cells that were incubated at 4° C., nor with IAA at 37° C. for additional 2 h or 4 h (FIG. 4c), further confirming the intracellular ATP-mediated drug release capability of Dox/NG.

Figure 11:
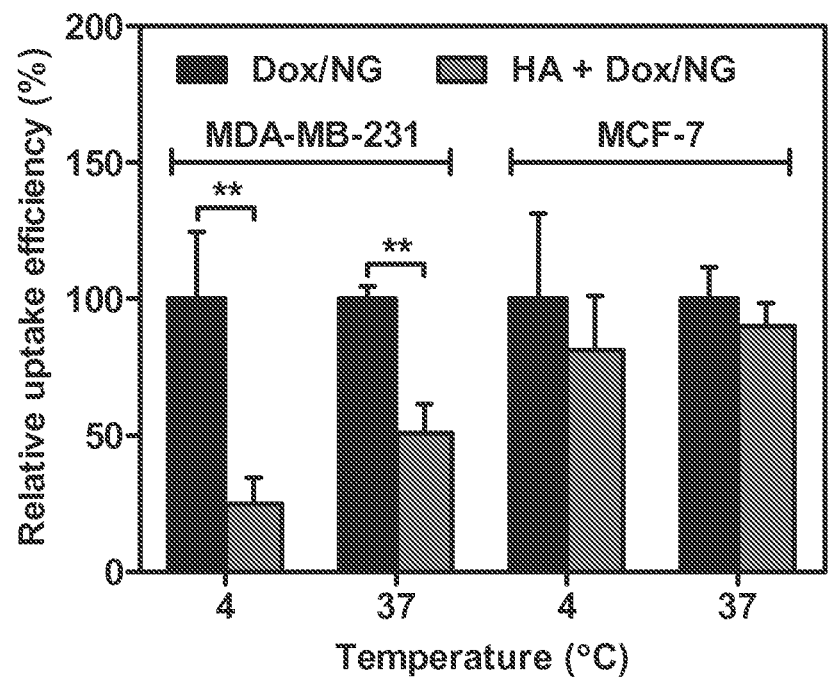
FIG. 11. Relative uptake efficiency of Dox/NG on MDA-MB-231 and MCF-7 cells in the presence of free HA at 4° C. and 37° C. **P<0.01. MDA-MB-231 cells compared with MCF-7 cells overexpress CD44 receptors. The cellular uptake of Dox/NG with HA was inferior to untreated on MDA-MB-231 cells regardless of the temperature. In contrast, insignificant differences were found in the cellular uptake of Dox/NG between MCF-7 cells treated with and without free HA. The results suggest that the decreased cellular uptake of Dox/NG on MDA-MB-231 cells was mainly attributed to the competitive binding of free HA to CD44 receptors instead of Dox/NG.
Figure 12:
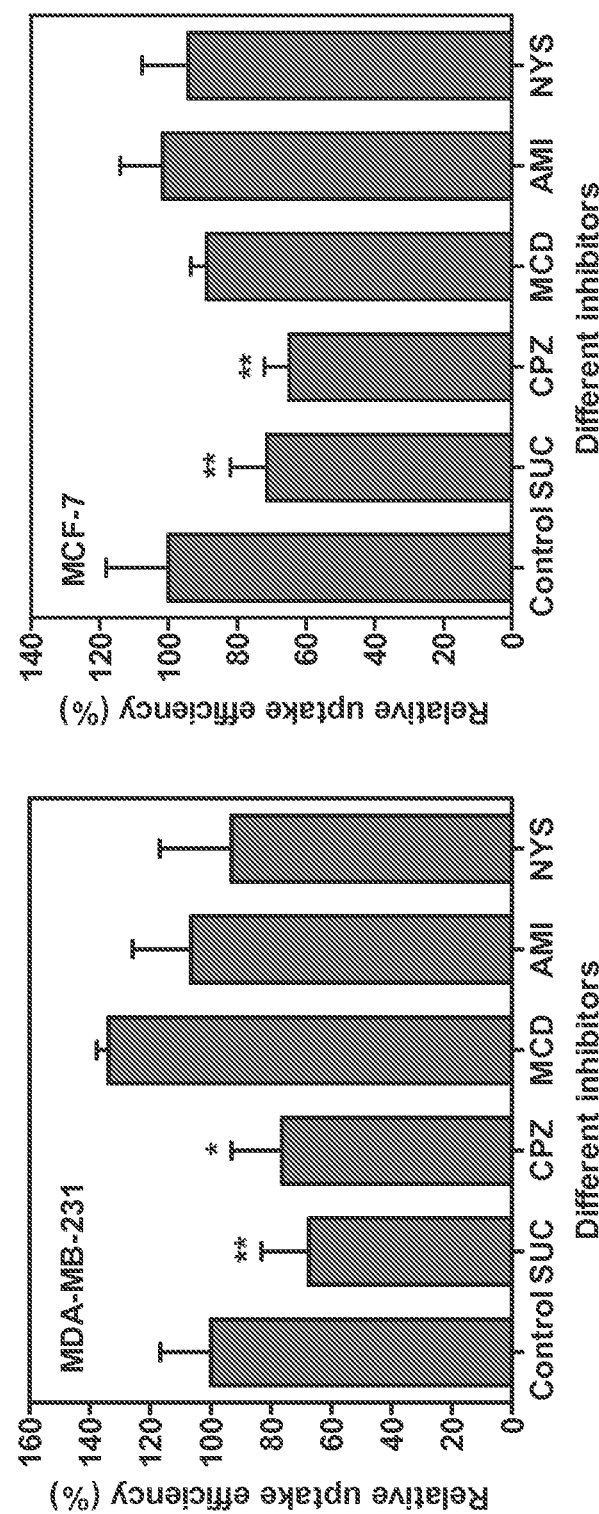
FIG. 12. Relative uptake efficiency of Dox/NG on MDA-MB-231 and MCF-7 cells in the presence of various endocytosis inhibitors. *P<0.05, **P<0.01. Inhibitor of clathrin-mediated endocytosis: sucrose (SUC) and chlorpromazine (CPZ); inhibitor of caveolin-mediated endocytosis: nystatin (NYS); inhibitor of macropinocytosis: amiloride (AMI); inhibitor of lipid raft: methyl-β-cyclodextrin (MCD). Compared with the cellular uptake of Dox/NG without inhibitors as a control, the significant decrease in uptake of Dox/NG with inhibitors confirmed the corresponding endocytosis pathways of the nanogels.

The intracellular delivery of Dox/NG in MDA-MB-231 cells was also explored using confocal laser scanning microscopy (CLSM). Dox/NG was demonstrated to bind to the CD44 receptor on the cell membrane (FIG. 11), followed by internalization via the clathrin-mediated pathway (FIG. 12) and subsequent transportation into the endosomes and lysosomes[42, 43]. As shown in FIG. 4d, most of the endocytosed Dox/NG was located in the endo-lysosomes judged by the yellow fluorescence during the first 2 h of incubation. However, after an additional 4 h of incubation, the conspicuous dissociation of the broader red fluorescence and less green fluorescence suggested the endo-lysosomal escape of Dox/NG with the help of protamine, and led to a significant release of Dox resulting from the high cytosolic ATP level. Furthermore, the released Dox specifically accumulated into the nuclei, as evidenced by the magenta fluorescence characteristic of a cascade in apoptosis.

Figure 13:
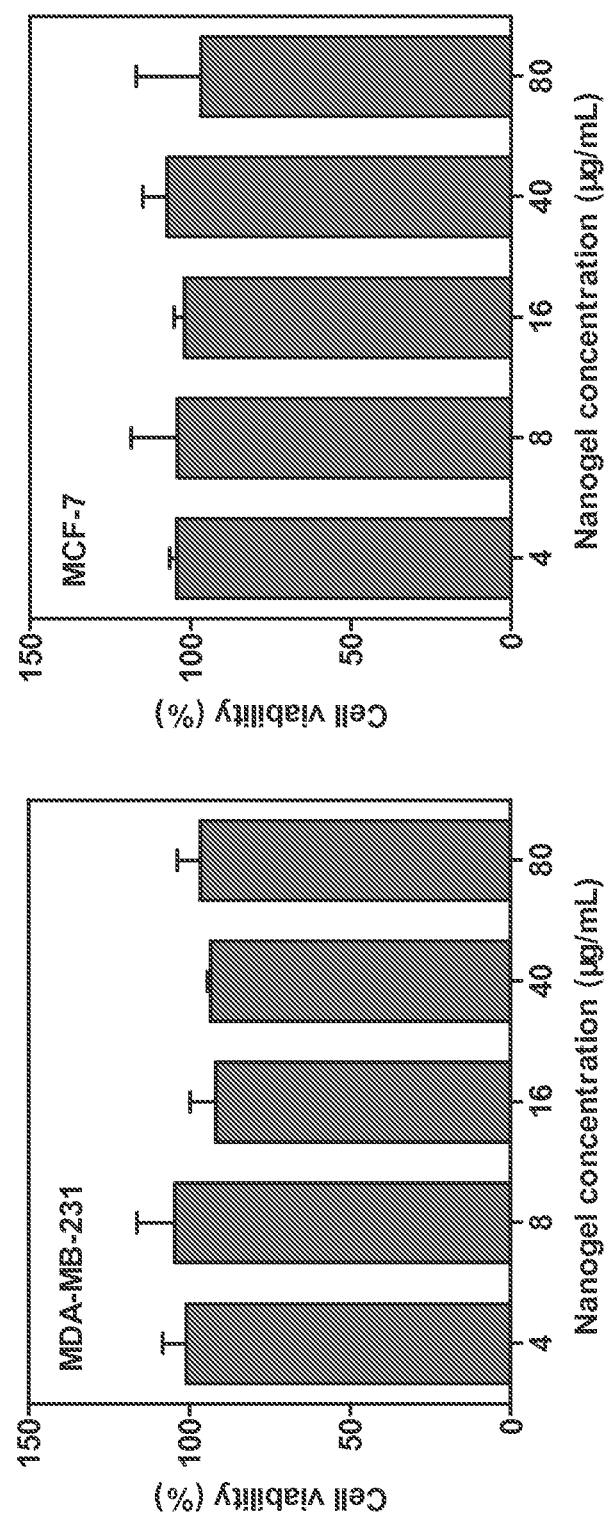
FIG. 13. In vitro cytotoxicity of blank ATP-responsive nanogels on MDA-MB-231 and MCF-7 cells for 24 h.

The in vitro cytotoxicity of Dox/NG against two kinds of human breast adenocarcinoma cells, specifically MDA-MB-231 and MCF-7 cells, was evaluated by using the 3-(4, 5-dimethylthiazol-2-yl)-2, 5-diphenyltetrazolium bromide (MTT) assay. Dox/NG presented the significantly enhanced cytotoxicity compared with Dox/cNG toward both MDA-MB-231 and MCF-7 cells at all the Dox concentrations studied (FIG. 4e, f). The half-maximal inhibitory concentration ($IC_{50}$) of Dox/NG was 0.24 µM on MDA-MB-231 cells and 0.80 µM on MCF-7 cells, which were remarkably lower than that of Dox/cNG, 1.1 µM on MDA-MB-231 cells and 2.9 µM on MCF-7 cells, respectively. Blank nanogels without Dox did not show toxicity within the tested range of concentrations (FIG. 13). Furthermore, Dox/NG was demonstrated to exert a higher apoptosis-inducing effect than Dox/cNG on MDA-MB-231 cells using the Annexin-FITC apoptosis detection assay (FIG. 4g). Additionally, in the terminal deoxynucleotidyl transferase dUTP nick end labeling (TUNEL) assay, MDA-MB-231 cells treated with Dox/NG showed more extensive apoptotic DNA fragmentation stained as green fluorescence in comparison with that treated with Dox/cNG (FIG. 4h). These results validated that ATP-responsive Dox/NG is an effective intracellular nanocarrier delivery system for enhanced anticancer activity.

In Vivo Tumor Targeting Delivery and Antitumor Activity of Dox/NG.

Figure 5:
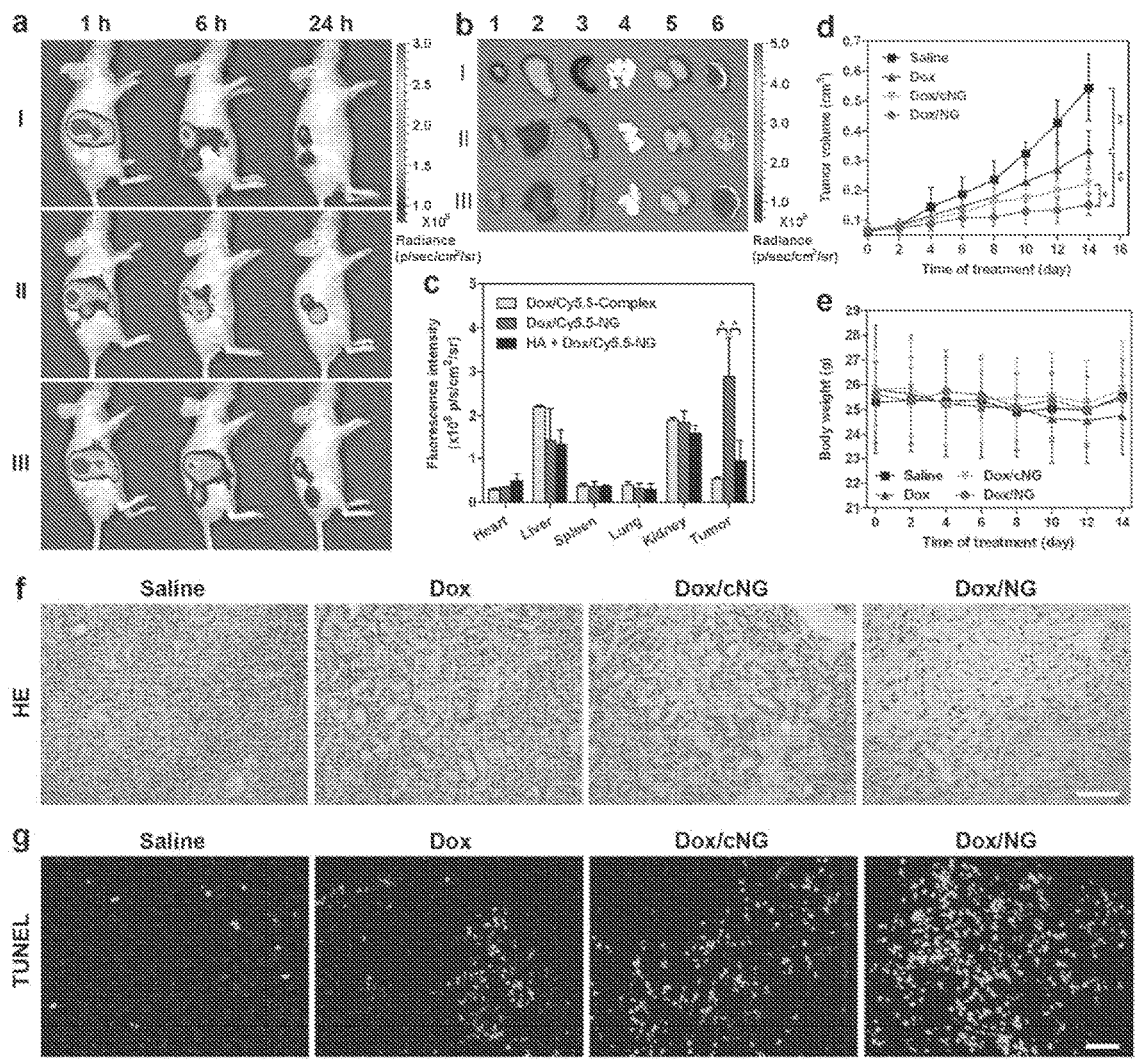
FIG. 5. In vivo tumor targeting delivery and antitumor activity. (a) In vivo fluorescence imaging of MDA-MB-231 tumor-bearing nude mice at 1, 6, and 24 h after intravenous injection of Dox/Cy5.5-Complex (I), Dox/Cy5.5-NG (II) and Dox/Cy5.5-NG with pre-injection of free HA (III) at Cy5.5 dose of 30 nmol/kg. Arrows indicate the sites of tumors. (b) Ex vivo fluorescence imaging of the tumor and normal tissues of MDA-MB-231 tumor-bearing nude mice after mice were euthanized at 24 h post injection. The numeric label for each organ is as follows: 1, heart; 2, liver; 3, spleen; 4, lung; 5, kidney; 6, tumor. (c) ROI analysis of fluorescent signals from the tumors and normal tissues. *P<0.05. (d) The MDA-MB-231 tumor growth curves after intravenous injection of different formulations of Dox at a dose of 2 mg/kg. *P<0.05, **P<0.01. (e) The body weight variation of MDA-MB-231 tumor-bearing mice during treatment. (f) Histological observation of the tumor tissues after treatment. The tumor sections were stained with HE. Scale bar is 100 μm. (g) Detection of apoptosis in the tumor tissues after treatment. The tumor sections were stained with fluorescein-dUTP (green) for apoptosis and Hoechst for nuclei (blue). Scale bar is 200 μm.

To evaluate the tumor targeting capability of Dox/NG, the in vivo biodistribution of Cy5.5-labeled Dox/NG (Dox/Cy5.5-NG) administrated intravenously into MDA-MD-231 tumor-bearing mice was investigated by a non-invasive near infrared optical imaging technique. As shown in FIG. 5a, Dox/Cy5.5-NG a presented a stronger fluorescence signal in the tumor region over a short time compared with Cy5.5-labeled Dox/Complex (Dox/Cy5.5-Complex) without the HA shell. As time increased, elevated fluorescence signals of Dox/Cy5.5-NG were found at the tumor site as compared to the normal tissues within 24 h post-injection, indicating a notable tumor targeting effect of the nanogels. To further confirm the role of the interaction between CD44 receptors and HA in this high tumor targetability of the nanogels, a high dose of free HA was intravenously pre-injected prior to administration of Dox/Cy5.5-NG to block CD44 mediated binding of the nanogels on tumor tissue. As expected, the fluorescence signal of Dox/Cy5.5-NG significantly reduced at the tumor site after pre-injection of free HA into the mice (FIG. 5a). After 24 h at post-injection, the mice were immediately euthanized, and the tumors as well as normal tissues were harvested for ex vivo imaging. The fluorescence signal of Dox/Cy5.5-NG at the tumor site was significantly higher than that of Dox/Cy5.5-Complex and Dox/Cy5.5-NG pretreated with free HA (FIG. 5b), which was sextupled and tripled using quantitative region-of-interest (ROI) analysis, respectively (FIG. 5c). In addition, the fluorescence signal at the tumor site was approximately double that in the liver or kidney after injection of Dox/Cy5.5-NG for 24 h (FIG. 5b, c). It was validated that the ATP-responsive nanogels had high tumor targetability due to a combination of passive and active targeting mechanisms.

Figure 14:
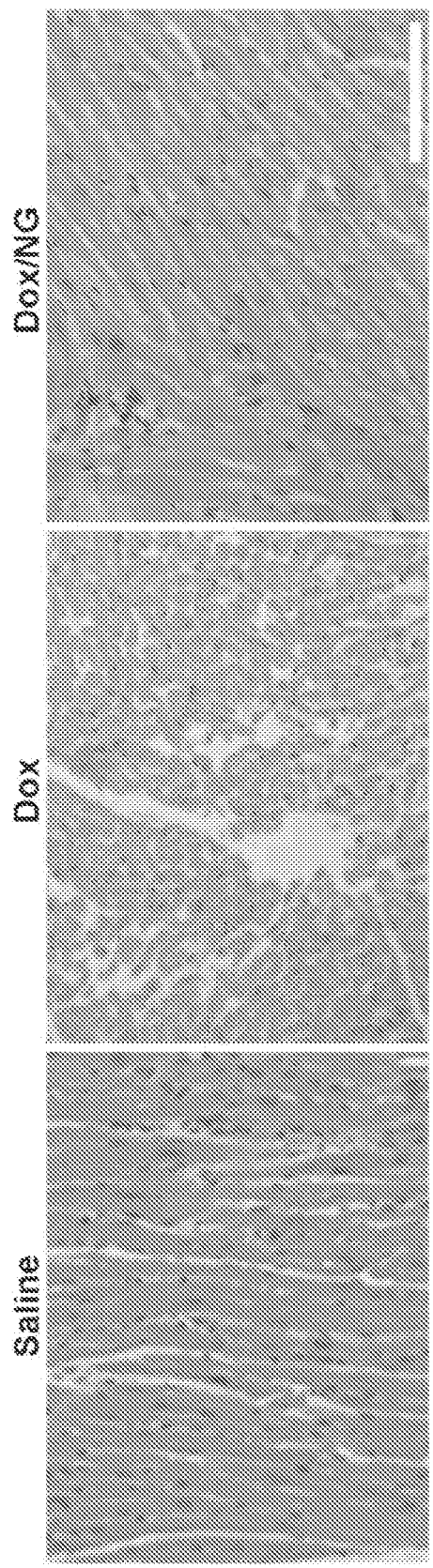
FIG. 14. Histological observation of the hearts of MDA-MB-231 tumor-bearing mice after treatment at Day 14. The heart sections were stained with HE. Scale bar is 100 μm.

To confirm the feasibility of the nanogels for cancer therapy in vivo, the antitumor efficacy of Dox/NG was estimated in MDA-MB-231 tumor xenograft models. As shown in FIG. 5d, different Dox formulations had significant effects on inhibiting tumor growth compared with saline as a negative control after successive intravenous administration into the tumor-bearing mice. Both Dox/cNG and Dox/NG presented remarkably higher inhibition efficacy toward tumor growth than the Dox solution, which primarily resulted from the tumor targeting capability of these nanogels. More importantly, a noticeable difference in tumor-size inhibition between Dox/NG and Dox/eNG was observed (FIG. 5d), suggesting that the efficient intracellular delivery and ATP-triggered Dox release are of great importance to enhanced antitumor activity. The body weights of the mice had no significant change during the treatment of Dox/NG (FIG. 5e). The histologic images using hematoxylin and eosin (HE) staining showed that after applying Dox/NG, a massive cancer cell remission occurred in the tumor tissue (FIG. 5f) while producing no obvious pathological abnormalities in the heart, such as cardiomyopathy, the main toxic effect in Dox cancer treatment[44] (FIG. 14). Moreover, the images obtained using in situ TUNEL assay showed the highest level of cell apoptosis in the tumor harvested from the mice treated with Dox/NG (FIG. 5g), indicating that the dominant inhibition activity of tumor growth was attributable in part to the increased apoptosis effect induced by Dox/NG. Collectively, these results verified that ATP-responsive Dox/NG efficiently accumulated at the tumor site, demonstrated effective intracellular transport and ATP-mediated drug release, and thereby achieved optimal antitumor efficacy in vivo.

Discussion

We successfully developed an ATP-responsive anticancer drug delivery system consisting of an all-biopolymer nanogel, with DNA, protein and polysaccharide. Our nanocarriers show drug release properties correlated to ATP levels, which selectively release the encapsulated Dox at high ATP levels for enhanced biological specificity and therapeutic efficacy in cancer therapy. We anticipate that this strategy will provide new opportunities for utilizing ATP as a metabolic trigger, which can lead to the development of increasingly specific drug delivery systems. Here Dox was intercalated in the GC-rich pairs of the DNA motif; however, other drugs[45-47] could also be loaded into the DNA chain through their specific affinity and be released by ATP's invasion. Alternatively, drugs can be encapsulated into nanocarriers "caged" by ATP aptamer for reversibly controlling drug release upon ATP's trigger. Furthermore, the intracellular level of ATP can be tuned by adjusting other metabolic elements' concentration or activity, such as glucose level, hydrogen ion gradient and oxidative stress[48-50]. The integration of these elements' synergistic efforts may result in a creation of novel families of metabolism based nano-machineries for transporting and activating a variety of cargos with programmable functions.

Methods

Preparation and Characterization of Dox-Loaded Nanogels.

100 µL of m-Protamine (0.7 mg/mL) was mixed with 100 µL of Dox/Duplex (0.85 mg/mL) and incubated for 10 min. The complex (Dox/Complex) was added into 200 µL of m-HA (0.35 mg/mL) solution with stirring, followed by adding glycerol dimethacrylate (GDA) (0.07 mg). Radical polymerization was photoinitiated by irgacure 2959 (0.1%, w:v) under the exposure to the ultraviolet radiation at the intensity of c.a. 20 mV/cm$^2$ for 60 s using a BlueWave 75 UV Curing Spot Lamp (DYMAX). Finally, the resulting Dox-loaded nanogels (Dox/NG) were obtained by washing with nuclease free water using centrifugal filter units (3K MWCO) (Millipore) to remove the excessive crosslinker and initiator. The particle size and zeta potential were measured by the Zetasizer (Nano ZS, Malvern). For transmission electron microscope (TEM) characterization, Dox/NG was dropped onto a TEM copper grid (300 mesh) (Ted Pella) and then stained with 1% phosphotungstic acid for 1 min. After air-dry, the sample was observed by TEM (JEM-2000FX, Hitachi) operating at 80 kV.

In Vitro ATP-Triggered Dox Release.

0.5 mL of Dox/NG with 14 µg Dox was added into a dialysis tube (10K MWCO) (Slide-A-Lyzer, Thermo Scientific) against 14 mL of the HEPES buffer solution (5 mM HEPES, 10 mM $MgCl_2$, pH 7.4) containing different concentrations of ATP, and gently shaken at 37° C. in a shaker (New Brunswick Scientific) at 100 rpm. At predetermined time intervals, the total buffer solution was withdrawn, followed by replacing with 14 mL of fresh buffer solution with the same ATP concentration. The fluorescence intensity of Dox released was measured at 596 nm with an excitation wavelength of 480 nm by a microplate reader (Infinite M200 PRO, Tecan).

Cell Culture.

MDA-MB-231 and MCF-7 cells were cultured in DMEM with 10% (v:v) FBS, 100 U/mL penicillin and 100 µg/mL streptomycin in an incubator (Thermo Scientific) at 37° C. under an atmosphere of 5% $CO_2$ and 90% relative humidity. The cells were sub-cultivated approximately every 3 days at 80% confluence using 0.25% (w:v) trypsin at a split ratio of 1:5.

ATP-Dependent Dox Release in the Cells.

MDA-MB-231 cells ($1 \times 10^5$ cells/well) were seeded in 6-well plates. After culture for 48 h, the cells were incubated with Dox-loaded nanogels (2 µM Dox concentration) for 2 h at 37° C. Then, the excessive nanogels were removed and the cells were incubated with fresh FBS free culture medium at 37° C. for additional 2 h or 4 h. After washing the cells by 4° C. PBS twice, the fluorescence intensity of Dox in the cells and the cell proteins were measured, respectively. Low temperature (4° C.) and iodoacetic acid (IAA) were used to inhibit ATP production in the cells. The content of ATP in the cells was assayed by the ATPlite Assay Kit (Perkin Elmer). After cell incubation with Dox/NG (2 µM Dox concentration) for 2 h at 37° C., the excessive nanogels were removed and the cells were incubated at 4° C. or with IAA (100 µM) at 37° C. for additional 2 h or 4 h. After washing the cells by 4° C. PBS twice, the fluorescence intensity of Dox in the cells was measured at 596 nm with an excitation wavelength of 480 run, which was normalized by subtracting the background signal of the blank cells. The cell proteins were assayed by the Pierce BCA protein assay kit (Thermo Scientific). Uptake of Dox was calculated as: Uptake of Dox (ng/mg)=$Q_{Dox}/Q_{cells\ protein}$, where $Q_{Dox}$ and $Q_{cells\ protein}$ were the amounts of Dox and cells protein, respectively.

Intracellular Trafficking.

MDA-MB-231 cells ($1\times10^5$ cells/well) were seeded in a confocal microscopy dish (MatTek). After culture for 24 h, the cells were incubated with Dox/NG (2 µM Dox concentration) at 37° C. for 2 h, and then washed by 4° C. PBS twice, followed by incubation with fresh FBS free culture medium for additional 0 h or 4 h. Subsequently, the cells were stained by LyosTracker Green (50 nM) (Life Technologies) at 37° C. for 30 min and Hoechst 33342 (1 µg/mL) (Life Technologies) at 37° C. for 10 min. Finally, the cells were washed by 4° C. PBS twice and immediately observed using CLSM (LSM 710, Zeiss).

In Vitro Cytotoxicity.

MDA-MB-231 or MCF-7 cells ($1\times10^4$ cells/well) were seeded in 96-well plates. After culture for 24 h, the cells were exposed to the Dox solution and Dox-loaded nanogels with different concentrations of Dox for 24 h, followed by adding 20 µL of the MTT solution (5 mg/mL). After 4 h of incubation, the medium was removed, and the cells were mixed with 150 µL of dimethyl sulfoxide (DMSO). The absorbance was measured at a test wavelength of 570 nm and a reference wavelength of 630 nm by a microplate reader (Infinite M200 PRO, Tecan).

Apoptosis Assay.

Apoptosis of MDA-MB-231 was detected using the APO-BrdU TUNEL Assay Kit (Life Technologies) and Annexin V-FITC Apoptosis Detection Kit (BD Biosciences), respectively. The cells ($1\times10^5$ cells/well) were seeded in 6-well plates. After culture for 48 h, the cells were incubated with Dox-loaded nanogels for 12 h (Annexin V-FITC) or 20 h (TUNEL). The subsequent procedures were performed in accordance with the manufacturer's protocol, respectively. For Annexin V-FITC apoptosis detection, the cells were analyzed by flow cytometry (BD FACSCalibur), while for TUNEL assay, the cells were observed by fluorescence microscope (IX71, Olympus).

Animals and Tumor Xenograft Models.

All animals were treated in accordance with the Guide for Care and Use of Laboratory Animals, approved by local committee. To set up the tumor xenograft model, the female nude mice were subcutaneously inoculated in the back with $1\times10^7$ MDA-MB-231 cells. The tumor size was monitored by a vernier caliper and the tumor volume (V) was calculated as $V=L\times W^2/2$, where L and W were the length and width of the tumor, respectively.

In Vivo Imaging Study.

When the tumors reached to 200-400 mm³, the mice were intravenously injected by Dox/Cy5.5-Complex and Dox/Cy5.5-NG at Cy5.5 dose of 30 nmol/kg, respectively. For HA competitive study, the mice were pre-injected by a high dose of free HA (50 mg/kg), and after 30 min, were injected by Dox/Cy5.5-NG. Images were taken on IVIS Lumina imaging system (Caliper, USA) at 1, 4 and 24 h post injection. After the 24 h scanning, the mice were euthanized. The tumors as well as major organs were harvested, weighed and subjected for ex vivo imaging. ROIs were circled around the organs, and the fluorescence intensities were analyzed by Living Image Software.

In Vivo Antitumor Efficacy.

The tumor-bearing mice were weighed and randomly divided into different groups when the tumor volume reached to 50 mm³. From Day 0, the mice were intravenously injected with Dox solution (2 mg/kg), Dox-loaded nanogels (2 mg/kg) and saline as a negative control every other day for 12 days, and meanwhile the tumor size was measured. At Day 14, the mice were euthanized, and the tumor as well as heart were collected, weighed, washed by saline thrice and fixed in the 10% neutral buffered formalin (NBF). For the HE staining, formalin-fixed tumors and hearts were embedded in paraffin blocks and visualized by optical microscope (DM5500B, Leica). For the TUNEL apoptosis staining, the fixed tumor sections were stained by the In Situ Cell Death Detection Kit (Roche Applied Science) according to the manufacturer's protocol. Hoechst 33342 was used for nuclear counterstaining. The stained tumor slides were observed by fluorescence microscope (IX71, Olympus).

Statistical Analysis.

Data are given as mean± standard deviation. Statistical significance was tested by two-tailed Student's t-test or one-way ANOVA. Statistical significance was set at *$P<0.05$, and extreme significance was set at **$P<0.01$.

BACKGROUND AND EXAMPLE 1
REFERENCES

1. Peer, D. et al. Nanocarriers as an emerging platform for cancer therapy. *Nat. Nanotechnol.* 2, 751-760 (2007),
2. Petros, R. A. & DeSimone, J. M. Strategies in the design of nanoparticles for therapeutic applications. *Nat. Rev. Drug Discov.* 9, 615-627 (2010).
3. Shi, J. J., Votruba, A. R., Farokhzad, O. C. & Langer, R. Nanotechnology in drug delivery and tissue engineering: from discovery to applications. *Nano Lett.* 10, 3223-3230 (2010).
4. Hrkaeh, J. et al. Preclinical development and clinical translation of a PSMA-targeted docetaxel nanoparticle with a differentiated pharmacological profile. *Sci. Transl. Med.* 4 (2012).
5. Allen, T. M. Ligand-targeted therapeutics in anticancer therapy. *Nat. Rev. Cancer* 2, 750-763 (2002).
6. Rapoport, N. Physical stimuli-responsive polymeric micelles for anti-cancer drug delivery. *Prog. Polym. Sci.* 32, 962-990 (2007).
7. Choi, S.-W., Zhang, Y. & Xia, Y. A Temperature-sensitive drug release system based on phase-change materials. *Angew. Chem., Int. Ed.* 49, 7904-7908 (2010).
8. Lee, H. I. et al. Light-induced reversible formation of polymeric micelles. *Angew. Chem., Int. Ed.* 46, 2453-2457 (2007).
9. Oliveira, H. et al. Magnetic field triggered drug release from polymersomes for cancer therapeutics. *J. Controlled Release* 169, 165-170 (2013).
10. Hernot, S. & Klibanov, A. L. Microbubbles in ultrasound-triggered drug and gene delivery. *Adv. Drug Deliv. Rev.* 60, 1153-1166 (2008).
11. Kwon, I. C., Bae, Y. H. & Kim, S. W. Electrically credible polymer gel for controlled release of drugs. *Nature* 354, 291-293 (1991).
12. Ke, C. J. et al. Smart multifunctional hollow microspheres for the quick release of drugs in intracellular lysosomal compartments. *Angew. Chem, Int. Ed.* 50, 8086-8089 (2011).
13. Ong, W., Yang, Y., Cruciano, A. C. & McCarley, R. L. Redox-triggered contents release from liposomes. *J. Am. Chem. Soc.* 130, 14739-14744 (2008).
14. Biswas, A. et al. Endoprotease-mediated intracellular protein delivery using nanocapsules. *ACS Nano* 5, 1385-1394 (2011).
15. Ravaine, V., Alicia, C. & Catargi, B. Chemically controlled closed-loop insulin delivery. *J. Controlled Release* 132, 2-11 (2008).

16. Gu, Z. et al. Injectable nano-network for glucose-mediated insulin delivery. *ACS Nano* 7, 4194-4201 (2013).
17. Torchilin, V. P. Recent advances with liposomes as pharmaceutical carriers. *Nat. Rev. Drug Discov.* 4, 145-160 (2005).
18. Motornov, M., Roiter, Y., Tokarev, I. & Minko, S. Stimuli-responsive nanoparticles, nanogels and capsules for integrated multifunctional intelligent systems. *Prog. Polym. Sci.* 35, 174-211 (2010).
19. Huang, H. C., Barua, S., Sharma, G., Dey, S. K. & Rege, K. Inorganic nanoparticles for cancer imaging and therapy. *J. Controlled Release* 155, 344-357 (2011).
20. Zhao, M. et al. Redox-responsive nanocapsules for intracellular protein delivery. *Biomaterials* 32, 5223-5230 (2011).
21. Knowles, J. R. Enzyme-catalyzed phosphoryl transfer-Reactions. *Annu. Rev. Biochem.* 49, 877-919 (1980).
22. Traut, T. W. Physiological concentrations of purines and pyrimidines. *Mol. Cell. Biochem.* 140, 1-22 (1994).
23. Leist, M., Single, B., Castoldi, A. F., Kuhnle, S. & Nicotera, P. Intracellular adenosine triphosphate (ATP) concentration: a switch in the decision between apoptosis and necrosis. *J. Exp. Med.* 185, 1481-1486 (1997).
24. Gorman, M. W., Feigl, E. O. & Buffington, C. W. Human plasma ATP concentration. *Clin. Chem.* 53, 318-325 (2007).
25. Gribble, F. M. et al. A novel method for measurement of submembrane ATP concentration. *J. Biol. Chem.* 275, 30046-30049 (2000).
26. Naito, M. et al. A phenylboronate-functionalized polyion complex micelle for ATP-triggered release of siRNA. *Angew. Chem., Int. Ed.* 51, 10751-10755 (2012).
27. Biswas, S. et al. Biomolecular robotics for chemomechanically driven guest delivery fuelled by intracellular ATP. *Nat. Chem.* 5, 613-620 (2013).
28. Liu, J. W. & Lu, Y. Smart nanomaterials responsive to multiple chemical stimuli with controllable cooperativity. *Adv. Mater.* 18, 1667-1671 (2006).
29. Zuo, X. L. et al. A target-responsive electrochemical aptamer switch (TREAS) for reagentless detection of nanomolar ATP. *J. Am. Chem. Soc.* 129, 1042-1043 (2007).
30. Pu, W. D., Zhang, L. & Huang, C. Z. Graphene oxide as a nano-platform for ATP detection based on aptamer chemistry, *Anal. Methods* 4, 1662-1666 (2012).
31. Wu, C. et al. Engineering of switchable aptamer micelle flares for molecular imaging in living cells. *ACS Nano* 7, 5724-5731 (2013).
32. Sorgi, F. L., Bhattacharya, S. & Huang, L. Protamine sulfate enhances lipid-mediated gene transfer. *Gene Ther.* 4, 961-968 (1997).
33. Gotte, M. & Yip, G. W. Heparanase, hyaluronan, and CD44 in cancers: a breast carcinoma perspective. *Cancer Res.* 66, 10233-10237 (2006).
34. Stern, R. & Jedrzejas, M. J. Hyaluronidases: their genomics, structures, and mechanisms of action. *Chem. Rev.* 106, 818-839 (2006).
35. Bertrand, P. et al. Increased hyaluronidase levels in breast tumor metastases. *Int. J. Cancer* 73, 327-331 (1997).
36. Yan, M. et al. A novel intracellular protein delivery platform based on single-protein nanocapsules. *Nat. Nanotechnol,* 5, 48-53 (2010).
37. Chaires, J. B., Herrera, J. E. & Waring, M. J. Preferential binding of daunomycin to 5'ATCG and 5'ATGC sequences revealed by footprinting titration experiments. *Biochemistry* 29, 6145-6153 (1990).
38. Kim, D., Jeong, Y. Y. & Jon, S. A drug-Loaded aptamer-gold nanoparticle bioconjugate for combined CT imaging and therapy of prostate cancer. *ACS Nano* 4, 3689-3696 (2010).
39. Xiao, Z. Y. et al. DNA self-Assembly of targeted near-infrared-responsive gold nanoparticles for cancer thermo-chemotherapy. *Angew. Chem., int. Ed.* 51, 11853-11857 (2012).
40. Brewer, L. R., Corzett, M. & Balhorn, R. Protamine-induced condensation and decondensation of the same DNA molecule. *Science* 286, 120-123 (1999).
41. Verrax, J., Dejeans, N., Sid, B., Glorieux, C. & Calderon, P. B. Intracellular ATP levels determine cell death fate of cancer cells exposed to both standard and redox chemotherapeutic agents. *Biochem. Pharmacal.* 82, 1540-1548 (2011).
42. Doherty, G. J. & McMahon, H. T. Mechanisms of endocytosis. *Annu. Rev. Biochem.* 78, 857-902 (2009).
43. Mo, R. et al. Multistage pH-responsive liposomes for mitochondrial-targeted anticancer drug delivery. *Adv. Mater.* 24, 3659-3665 (2012).
44. Takemura, G. & Fujiwara, H. Doxorubicin-induced cardiomyopathy from the cardiotoxic mechanisms to management. *Prog. Cardiovasc. Dis.* 49, 330-352 (2007).
45. Nicolaou, K. C. & Dai, W. M. Chemistry and biology of the enediyne anticancer antibiotics. *Angew. Chem., Int. Ed.* 30, 1387-1416 (1991).
46. Smith, C. K., Davies, G. J., Dodson, E. T. & Moore, M. H. DNA-nogalamycin interactions: the crystal-structure of D(TGATCA) complexed with nogalamycin. *Biochemistry* 34, 415-425 (1995).
47. Zheng, J. et al. A spherical nucleic acid platform based on self-assembled DNA biopolymer for high-performance cancer therapy. *ACS Nano* (2013).
48. Vander Heiden, M. G. Targeting cancer metabolism: a therapeutic window opens. *Nat. Rev. Drug Discov.* 10, 671-684 (2011).
49. Hamanaka, R. B. & Chandel, N. S. Targeting glucose metabolism for cancer therapy. *J. Exp. Med.* 209, 211-215 (2012).
50. Wilson, W. R. & Hay, M. P. Targeting hypoxia in cancer therapy. *Nat. Rev. Cancer* 11, 393-410 (2011).

EXAMPLE 1 SUPPLEMENTAL INFORMATION

Materials and Methods

Materials. All chemicals were purchased from Sigma-Aldrich unless otherwise specified, and were used as received. Hyaluronic acid (HA, 77 KDa) was purchased from Freda Biochem Co., Ltd. (Shandong, China). ATP aptamer, complementary single stranded DNA (cDNA) of ATP aptamer, control aptamer, cDNA of control aptamer, Cy5.5-Tabled cDNA of ATP aptamer were purchased from Integrated DNA Technologies, Inc. (Coralville, USA).

Sensitivity and Selectivity of Dox Release from ATP-Responsive DNA Scaffold.

The Dox-loaded ATP-responsive DNA duplex (Dox/Duplex) was prepared by incubating Dox with a hybridized duplex of ATP aptamer and its cDNA at a molar ratio of 1:1, 100 μL of Dox/Duplex (2 μM Dox concentration) was added with 5 μL of either ATP, CTP, GTP or UTP, followed by adding 45 μL of concentrated buffer to achieve a 5 mM HEPES buffer (pH 7.4) containing 10 mM $MgCl_2$ and 137 mM NaCl, and was subsequently incubated for 15 min. The fluorescence spectra of Dox were scanned at an excitation wavelength of 480 nm by a microplate reader (Infinite M200 PRO, Tecan).

Synthesis and Characterization of Protamine with Acrylamide Groups (m-Protamine).

10 mg of protamine in 4 mL of sodium carbonate buffer (NaHCO$_3$, 50 mM, pH 8.5) was reacted with 4 mg of N-acryloxysuccinimide in 40 ΞL of dimethyl sulphoxide (DMSO) for 2 h at room temperature. The reaction solution was thoroughly dialyzed against deionized (DI) water[1]. The concentration of m-Protamine was determined by the Bradford assay (Thermo Scientific). The molecular weight of protamine and m-Protamine obtained from matrix-assisted laser desorption/ionization-time of flight (MALDI-TOF) mass spectrum were 4225.62 and 4391.54, respectively. The degree of modification was calculated to be three acrylamide groups per protein.

Synthesis and Characterization of Hyaluronic Acid with Acrylate Groups (m-HA).

One gram hyaluronic acid (HA) was dissolved in 50 mL of DI water at 4° C., followed by dropwise addition of 0.8 mL of methacrylic anhydride (MA)[2]. The reaction solution was adjusted to pH 8-9 by the addition of 5 M sodium hydroxide (NaOH) with continuous stirring at 4° C. for 24 h. The polymer was then precipitated in acetone, washed by ethanol and re-dissolved in DI water. After dialysis against DI water for 48 h, m-HA was obtained with a yield of 87.5% by means of freeze-drying and characterized by $^1$H NMR (Varian Gemini 2300). The degree of modification was determined to be c.a. 15% by comparing the ratio of the areas under the proton peaks at 5.74 and 6.17 ppm (methacrylate protons) to the peak at 1.99 ppm (N-acetyl glucosamine of HA) after performing a standard deconvolution algorithm to separate closely spaced peaks.

m-HA: $^1$H NMR (D$_2$O, 300 MHz, δ ppm): 1.85-1.96 (m, 3H, CH$_2$=C(CH$_3$)CO), 1.99 (s, 3H, NHCOCH$_3$), 5.74 (s, 1H, CH$^1$H$^2$=C(CH$_3$)CO), 6.17 (s, 1H, CH$^1$H$^2$=C(CH$_3$)CO).

Degradation of HA Shell.

100 µL of Dox/NG was incubated with 400 µL, of 0.5 mg/mL hyaluronidase (HAase) at different pH values and was sampled at predetermined time intervals. The zeta potentials of these samples were measured by a Zetasizer (Nano ZS, Malvern).

CD44 Receptor Targeting.

MDA-MB-231 and MCF-7 cells (1×10$^5$ cells/well) were seeded in 6-well plates. After culture for 48 h, the cells were pre-incubated with HA (5 mg/mL) for 2 h at 4° C. or 37° C., and then with Dox/NG (2 µM Dox concentration) in the presence of HA for another 2 h. Subsequently, the solution was removed, and the cells were washed by 4° C. PBS twice. The fluorescence intensity of Dox in the cells was measured, which was normalized by subtracting the background signal of the blank cells. The cell proteins were assayed by the Pierce BCA protein assay kit (Thermo Scientific). Uptake of Dox was calculated as: Uptake of Dox (ng/mg)=$Q_{Dox}/Q_{protein}$, where $Q_{dox}$ and $Q_{protein}$ were the amounts of Dox and cellular protein, respectively.

Determination of Endocytosis Pathways.

MDA-MB-231 and MCF-7 cells (1×10$^5$ cells/well) were seeded in 6-well plates. After culture for 48 h, the cells were pre-incubated with several specific inhibitors for various kinds of endocytosis [inhibitor of clathrin-mediated endocytosis: sucrose (SUC, 450 mM)[3] and chlorpromazine (CPZ, 10 µM)[4]; inhibitor of caveolin-mediated endocytosis: nystatin (NYS, 25 µg/mL)[5]; inhibitor of macropinocytosis: amiloride (AMI, 1 mM)[6]; inhibitor of lipid raft: methyl-β-cyclodextrin (MCD, 3 mM)[7]] for 1 h at 37° C., respectively. Afterwards, the cells were incubated with Dox/NG at a Dox concentration of 2 µM in the presence of inibitors for additional 2 h. After washing the cells by 4° C. PBS twice, the fluorescence intensity of Dox in the cells and the cell proteins were measured, respectively.

TABLE 1

Synthesized oligonucleotides used in the experiments.

| Oligonucleotides | Sequence |
|---|---|
| ATP aptamer | 5'-ACC TGG GGG AGT ATT GCG GAG GAA GGT-3' (SEQ ID NO: 1) |
| cDNA of ATP aptamer | 5'-ACC TTC CTC CGC AAT ACT CCC CCA GGT-3' (SEQ ID NO: 2) |
| Cy5.5-labeled cDNA | 5'-Cy5.5-ACC TTC CTC CGC AAT ACT CCC CCA GGT-3' (SEQ ID NO: 3) |
| control aptamer | 5'-ACC TGG GGG AGT ATT GTA AAA AAG AAT-3' (SEQ ID NO: 4) |
| cDNA of control aptamer | 5'-ATT CTT TTT TAC AAT ACT CCC CCA GGT-3' (SEQ ID NO: 5) |

EXAMPLE 1 SUPPLEMENTAL REFERENCES

1. Yan, M. et al. A novel intracellular protein delivery platform based on single-protein nanocapsules. *Nat. Nanotechnol.* 5, 48-53 (2010).
2. Hachet, E., Van Den Berghe, H., Bayma, E., Block, M. R. & Auzely-Velty, R. Design of biomimetic cell-interactive substrates using hyaluronic acid hydrogels with tunable mechanical properties. *Biomacromolecules* 13, 1818-1827 (2012).
3. Mo, R. et al. Multistage pH-responsive liposomes for mitochondrial-targeted anticancer drug delivery. *Adv. Mater.* 24, 3659-3665 (2012).
4. Zhang, X.-X., Allen, P. G. & Grinstaff, M. Macropinocytosis is the major pathway responsible for DNA transfection in CHO cells by a charge-reversal amphiphile. *Mol. Pharmaceutics* 8, 758-766 (2011).
5. ur Rehman, Z., Hoekstra, D. & Zuhom, I. S. Protein kinase A inhibition modulates the intracellular routing of gene delivery vehicles in HeLa cells, leading to productive transfection. *J Controlled Release* 156, 76-84 (2011).
6. Koivusalo, M. et al. Amiloride inhibits macropinocytosis by lowering submembranous pH and preventing Rac1 and Cdc42 signaling. *J. Cell. Biol.* 188, 547-563 (2010).
7. Chiu, Y. L. et al. The characteristics, cellular uptake and intracellular trafficking of nanoparticles made of hydrophobically-modified chitosan. *J Controlled Release* 146, 152-159 (2010).

EXAMPLE 2

Sequential and Site-Specific Delivery of Dual Anticancer Therapeutics Using Programmed Nanodepots A programmed drug delivery system that can transport different anticancer therapeutics to their distinct targets holds vast promise for cancer treatment. Herein, we develop a core-shell based "nanodepot" consisting of a liposomal core and a crosslinked-gel shell (designated Gelipo) for the sequential and site-specific delivery (SSSD) of tumor necrosis factor (TNF)-related apoptosis-inducing ligand (TRAIL) and doxorubicin (Dox). As a small-molecule drug intercalating the nuclear DNA, Dox is loaded in the aqueous core of the liposome, while TRAIL acting on the death receptor (DR) on the plasma membrane is encapsulated in the outer shell made of crosslinked hyaluronic acid (HA). The degradation of the HA shell by HAase that is concentrated in the tumor environment results in the rapid extracellular release of TRAIL and subsequent internalization of the liposomes. The parallel activity of TRAIL and Dox show synergistic anticancer efficacy. The half-maximal inhibitory concentration ($IC_{50}$) of TRAIL and Dox co-loaded Gelipo (TRAIL/Dox-Gelipo) toward the human breast cancer (MDA-MB-231) cells is 86 ng/mL (Dox concentration), a 5.3-fold increase compared to that of Dox-loaded liposomes (Dox-R8H3-L). Moreover, Gelipo with the programmed choreography displays a remarkable tumor accumulation and significantly improving the inhibition of the tumor growth in the MDA-MB-231 xenograft tumor animal model.

Combination therapy holds considerable appeal in enhancement of antitumor activity by achieving synergistic effects and reducing toxicity, which has been proved to be more effective than monotherapy in preclinical and clinical cancer treatment.[1] However, the general administration of agent "cocktails" based combination therapy often suffers from distinct pharmacokinetic profiles of different therapeutics that lead to an inconsistent in vivo biodistribution and therefore an inefficient therapy.[2] To address this dilemma, the nanoparticle-based drug co-delivery systems, such as polymeric nanoparticles,[3] liposomes,[4] nanocomplex[5] and inorganic nanoparticles,[6] have been widely developed to unify the individual pharmacokinetic behavior of different drug cargos. Upon the enhanced permeability and retention (EPR) effect, a single nanocarrier preferentially transports the multiple therapeutic agents, either small-molecule drugs or macromolecular drugs with different antitumor mechanisms to the same destination.

The conventional chemotherapeutic drugs attack the tumors by interrupting processes or inhibiting substances essential for the replication and proliferation of the tumor cells. For example, co-delivery of doxorubicin (Dox) and paclitaxel (Ptx) by a polymeric nanoparticle[7] was able to release both drugs simultaneously and efficiently within the cells. The released Ptx inhibits the intracytoplasmic microtubules disassembly that is required for cell proliferation,[8] while Dox intercalates into the nuclear DNA and induced cell apoptosis.[9] For the cancer gene therapy, siRNA for silencing the target genes in cancer cells and pDNA for implanting corrective genetic material into the cells, have been applied to coordinate with small-molecule drugs.[3b, 5c] A typical example involves a micellar nanocarrier for co-delivery of MDR-1 siRNA and Dox, the released siRNA in the cells downregulates the P-glycoprotein expression to improve the efficacy of Dox in the multidrug-resistant cancer cells.[3b]

Protein therapeutics such as cytokines,[10] antibodies,[11] and transcription factors[12] are emerging anticancer strategies, typically based on two mechanisms: apoptosis signal activation[10c] and growth signal blockage.[13] Of note, these proteins have specific sites of activities, which are generally divided as the extracellular target on the cellular membrane and the intracellular object in the cells. For example, cytochrome c[14] and caspase 3[15] act in the cytosol to initiate activation of the caspase cascade for the intrinsic apoptosis pathway;[16] while some take effect by binding to the specific receptor on the plasma membrane, such as cetuximab to the human epidermal growth factor receptor (EGFR),[17] trastuzumab to the human epidermal growth factor receptor 2 (HER-2),[18] and tumor necrosis factor (TNF)-related apoptosis-inducing ligand (TRAIL) to the death receptor.[10b, 10c] However, a synergistic anticancer co-delivery system integrating membrane-associated proteins and intracellular-functioned small drugs still remains elusive.

Figure 15:
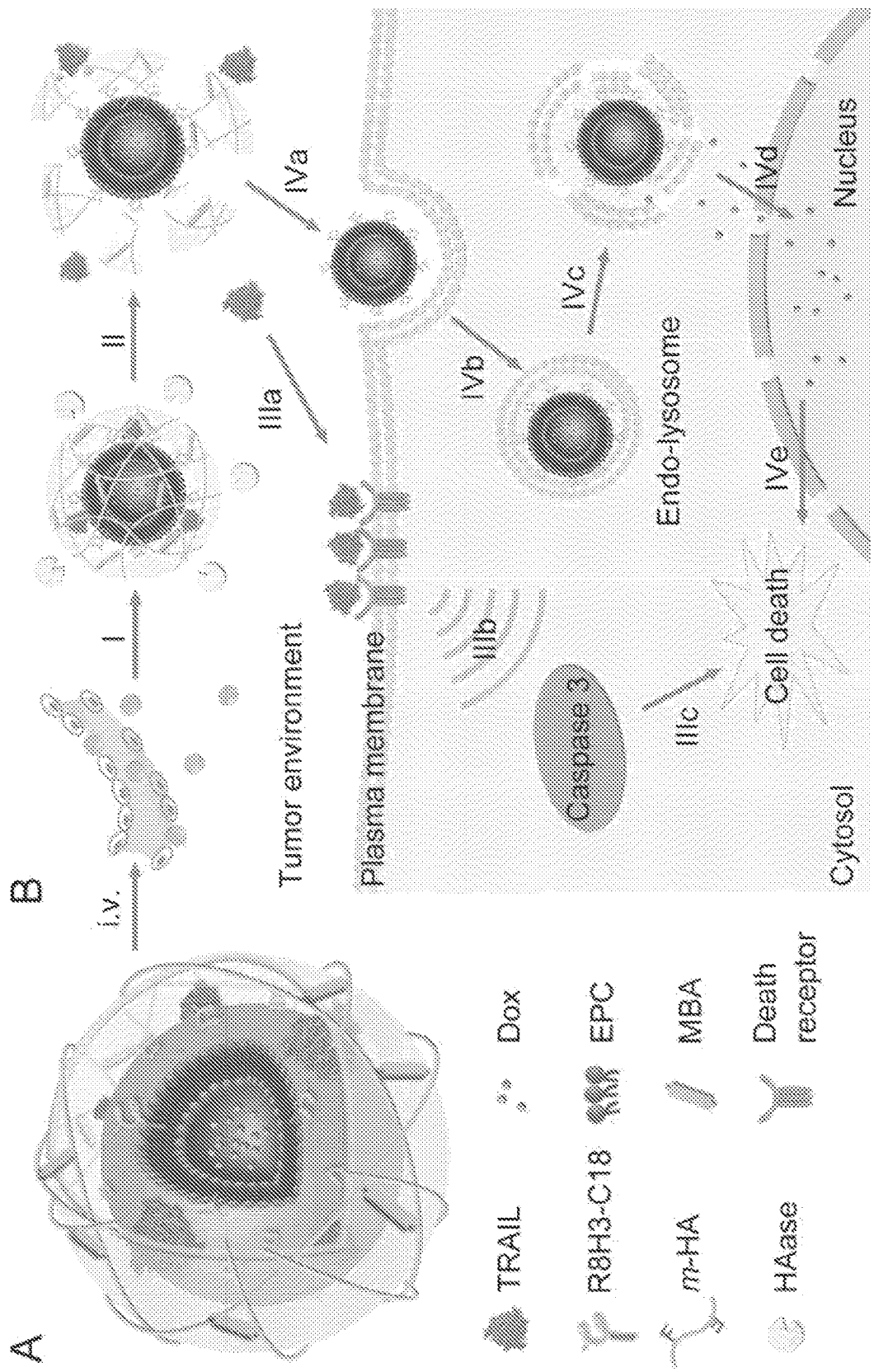
FIG. 15. Schematic design of TRAIL/Dox-Gelipo for sequential and site-specific drug delivery. A) The main components of TRAIL/Dox-Gelipo: R8H3 modified liposomal core loading Dox and crosslinked HA gel based outer shell encapsulating TRAIL. B) Sequential delivery of TRAIL to the plasma membrane and Dox to the nuclei by TRAIL/Dox-Gelipo for combination cancer treatment. I, accumulation of Gelipo (blue balls) at the tumor site through the passive and active targeting effects; II, degradation of HA crosslinked shell by HAase; IIIa, released TRAIL binding onto the death receptors on the plasma membrane; IIIb, activation of the caspase 3 signaling pathway; IIIc, induction of the cell death; IVa, exposure of R8H3 facilitating the tumor cellular uptake of Dox-R8H3-L; IVb, internalization of Dox-R8H3-L into the tumor cells; IVc, endo/lysosomal escape; IVd, accumulation of the released Dox into nucleus; IVe, intercalation of Dox on DNA inducing the cell death.

Herein, we report a novel core-shell based nano-vehicle for sequential and site-specific delivery (SSSD) of an anticancer protein and a small-molecule drug, which act on the cellular membrane and in the nucleus, respectively. As shown in FIG. 15A, to achieve a programmed release profile, a core-shell complex is designed to incorporate two separate depots: 1) liposome based inner core for loading the small-molecule drug and 2) crosslinked gel based outer shell for encapsulating the therapeutic protein. The materials used to compose these depots are tailored to arm with the stimuli-responsive elements that can be degraded or dissociated upon distinct tumor microenvironmental and cellular conditions. We therefore hypothesize that the obtained gel-lipsome complex (designated "Gelipo") undergoes sequential triggers to precisely release cargos into different specific sites. To demonstrate our hypothesis, two kinds of anticancer agents, Dox and TRAIL were applied. As a model small-molecule drug that functions by intercalating the nuclear DNA,[9] Dox is encapsulated in the aqueous core of the cell-penetrating peptide (CPP, R8H3) modified liposome (R8H3-L). TRAIL induces apoptosis primarily in the tumor cells by binding to certain death receptors (DR4, DR5) on the plasma membrane, while exhibiting insignificant toxicity to the normal cells.[19] Enzymatically degradable hyaluronic acid (HA) modified with acrylated pendants was utilized to adhere to the R8H3-L surface and subsequently encapsulate oppositely charged TRAIL into a photo-crosslinked matrix, which enhances protein stability, avoids denaturation in plasma, and shields from immunogenicity.[20] Furthermore, the HA shell also provides the active tumor targeting ligand to bind the overexpressing receptors on the cell surface of a variety of tumors, such as CD44.[21]

As displayed in FIG. 15B, after intravenous injection (i.v.) of TRAIL and Dox co-loaded Gelipo (TRAIL/DOX-Gelipo), Gelipo is expected to exhibit a considerable accumulation at the tumor site due to a combination of passive and active targeting mechanisms. At the tumor microenvironment, HAase, a specific enzyme has been proved to be highly expressed,[22] which promotes the degradation of the HA shell, thereby allowing the release of TRAIL and the exposure of R8H3-L. The extracellular released TRAIL binds to the cell death receptor on the plasma membrane, which can activate the cellular signaling to induce programmed cell death.[10b] On the other hand, the exposed positively charged R8H3 improves the internalization efficiency of the liposome into the tumor cells. When localized into endosomes and lysosomes (endo-lysosomes), Dox-R8H3-L is able to efficiently transport from the endo-lysosomes with the help of R8H3 possessing high-penetrating capability, accompanied by the release of Dox. The released Dox specifically accumulates into the nuclei for subsequent trigger of the apoptosis and cytotoxicity.[9, 23]

Results and Discussion

Preparation and Characterization of Gelipo.

Figure 16:
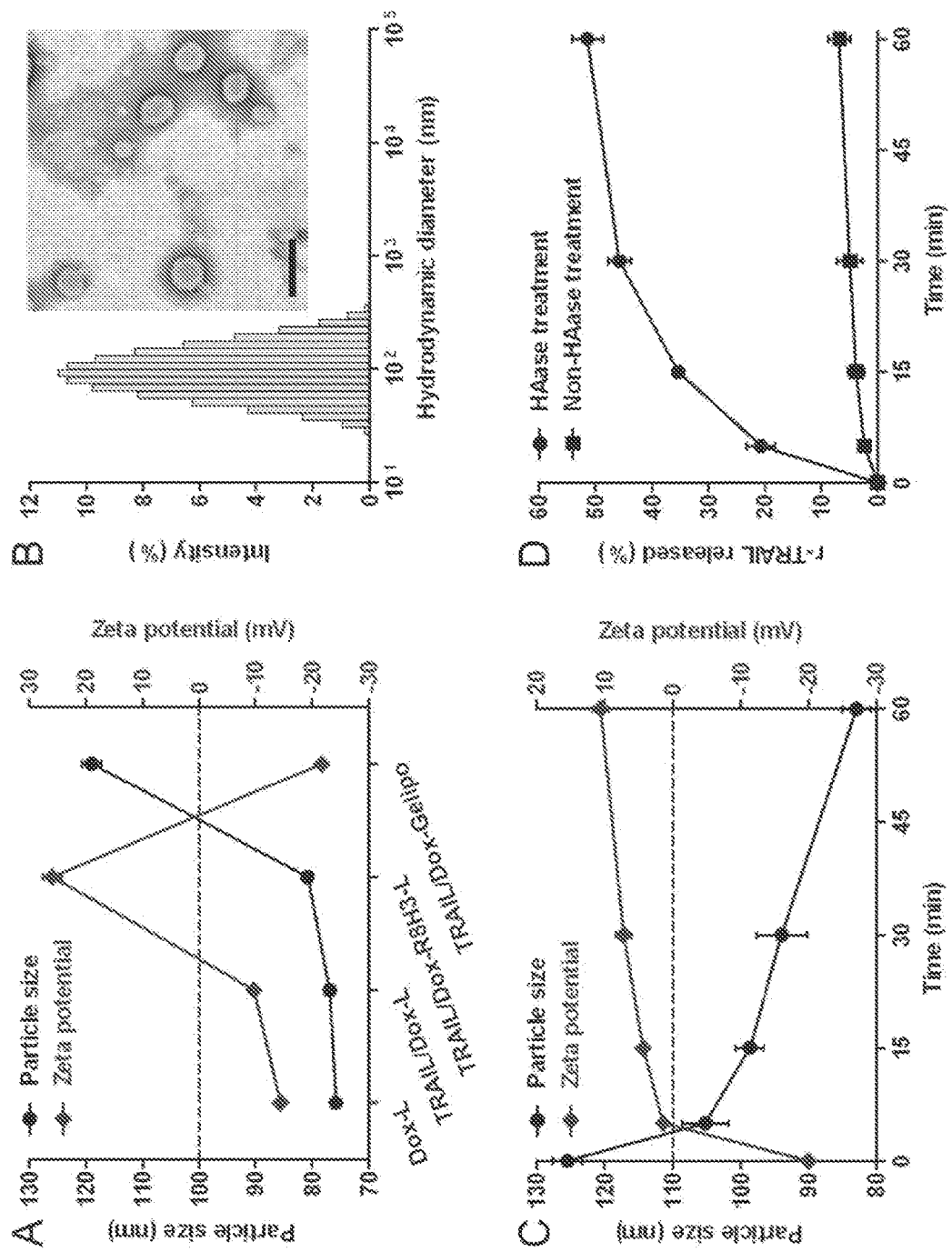
FIG. 16. A) The particle size and zeta potential of Dox-L, TRAIL/Dox-L, TRAIL/Dox-R8H3-L and TRAIL/Dox-Gelipo. B) The hydrodynamic size of TRAIL/Dox-Gelipo measured by dynamic light scattering (DLS). Inset: TEM image of TRAIL/Dox-Gelipo. Scale bar is 200 nm. C) Change in particle size and zeta potential of Gelipo incubated with HAase at pH 6.5 over time. D) In vitro release of r-TRAIL from r-TRAIL-Gelipo with and without HAase treatment.
Figure 20:
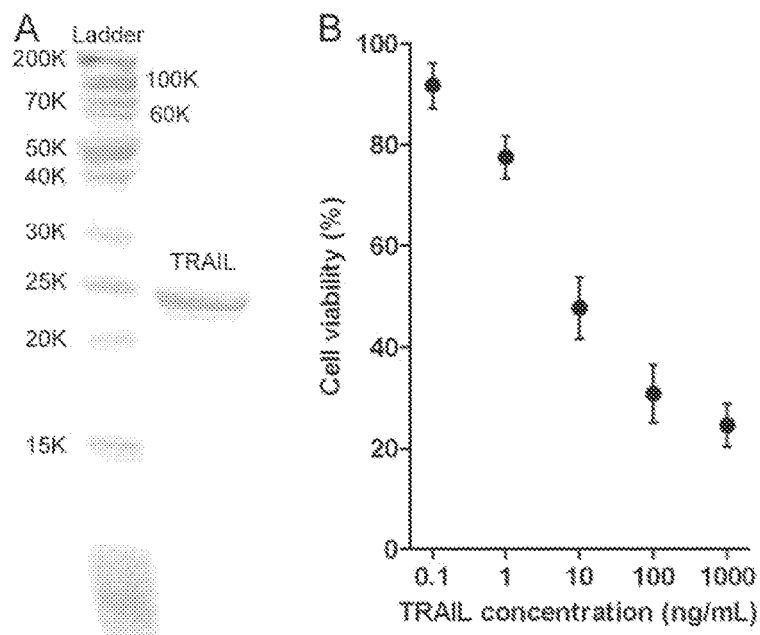
FIG. 20. (A) SDS-PAGE patterns of TRAIL (12% gel). TRAIL showed about 24 kDa molecular mass. (B) In vitro cytotoxicity of the obtained TRAIL on MDA-MB-231 cells for 24 h.
Figure 21:
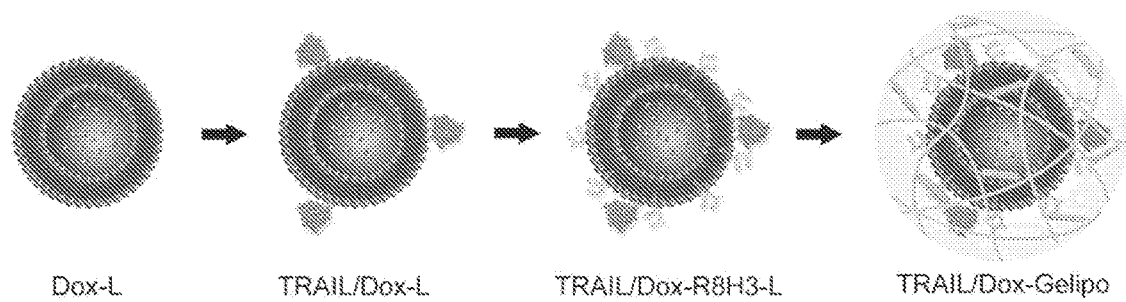
FIG. 21. Schematic design of the preparation of TRAIL/Dox-Gelipo.
Figure 22:
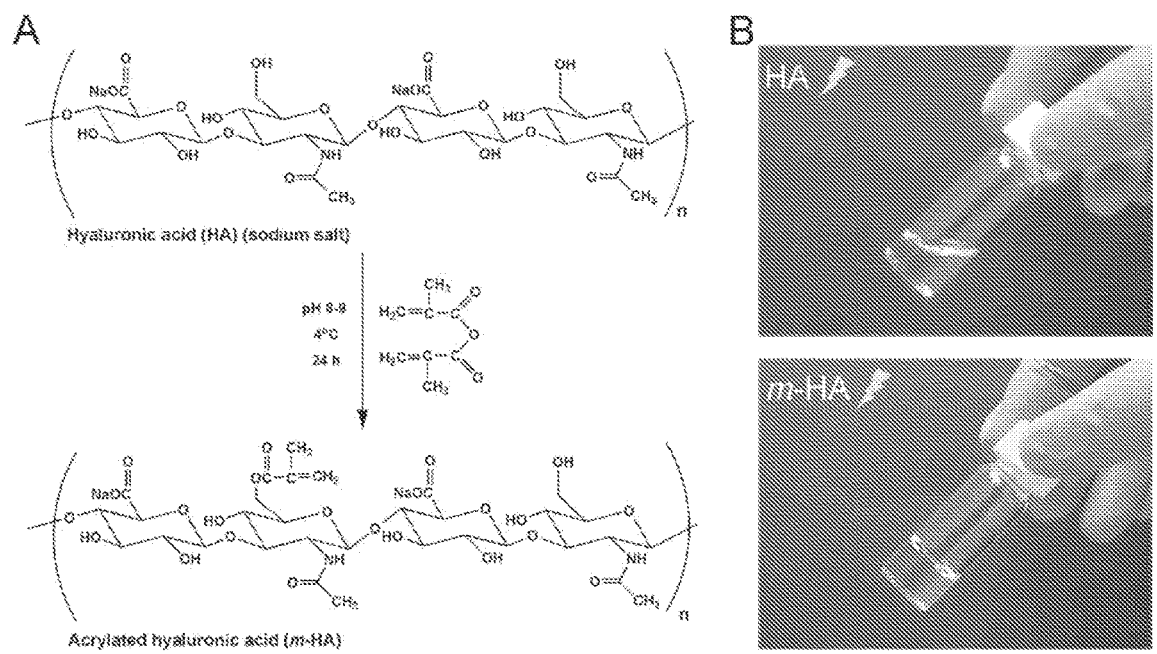
FIG. 22. (A) Synthesis of m-HA. (B) The hydrogel can be formed by m-HA (2%, w:v) (bottom) by Irgacure 2959 (0.1%, w:v) via UV irradiation for 30 s in contrast to HA with the same concentration (top).

We first prepared Dox-loaded liposomes (Dox-L) as the liposomal core of Gelipo by the transmembrane pH gradient method.[24] The drug-loading capacity and the encapsulation efficiency of Dox in Dox-L were about 5% and 99.5%, respectively, showing that Dox was efficiently encapsulated in the hydrophilic inner core of the liposomes. Dox-L had an average diameter of about 76 nm and a zeta potential of −14 mV (FIG. 16A). Next, the positively charged TRAIL with a molecular weight of about 24 KDa (FIG. 20) was attached onto the surface of negatively charged Dox-L via electrostatic absorption (TRAIL/Dox-L) (FIG. 21), which resulted in a slight decrease of the zeta potential to −10 mV. A synthesized cell penetrating peptide (R8H3) conjugated with a stearyl chain (R8H3-C18) was then anchored into the membrane of TRAIL/Dox-L by a combination of hydrophobic and electrostatic interactions[25] (TRAIL/Dox-R8H3-L) determined by a significant charge conversion from −10 mV of TRAILIDox-L to +26 mV of TRAIL/Dox-R8H3-L. Finally, TRAIL/DOX-Gelipo was obtained by adding TRAIL/Dox-R8H3-L into a solution with the negatively charged HA modified with polymerizable acrylate groups (designated m-HA) (FIG. 22) and crosslinker, N,N'-methylenebisacrylamide (MBA) followed by the interfacial polymerization[26] via UV irradiation for a short period of time. The notably increased particle diameter of 120 nm and a highly negative surface charge of −22 mV indicated the successful coating of the HA-crosslinked gel shell on the surface of the liposomal core. The encapsulation efficiency of TRAIL in TRAIL/Dox-R8H3-L was determined to be 82%. The transmission electron microscope (TEM) image showed a spheroid structure of TRAIL/Dox-Gelipo with a uniform particle size of about 110 nm (FIG. 16B).

Figure 23:
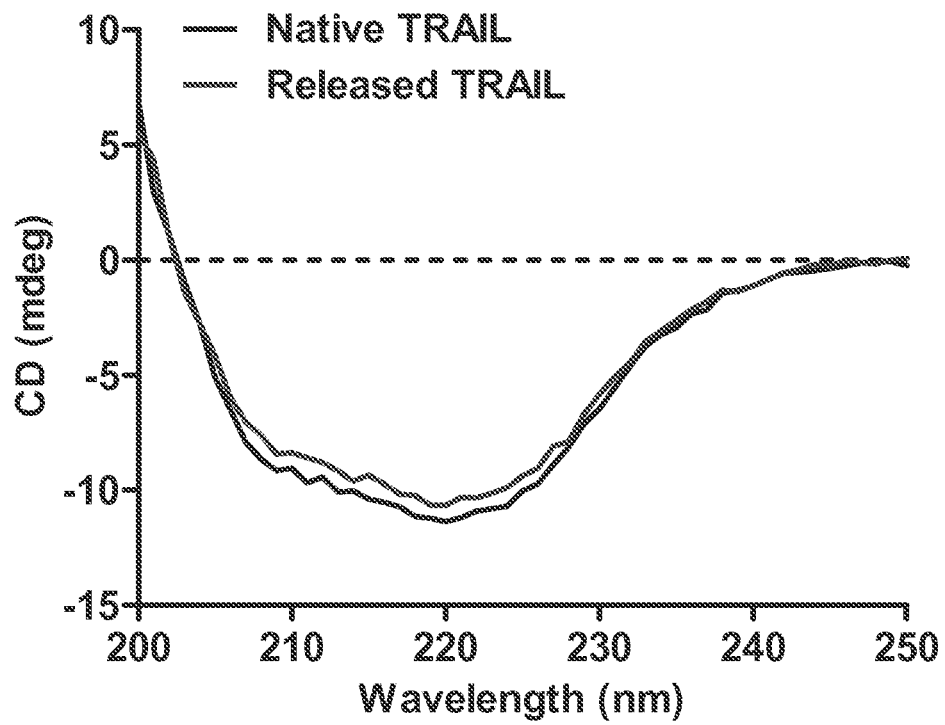
FIG. 23. Circular dichroism (CD) spectra of standard native TRAIL solution and TRAIL released from Gelipo.

To verify the degradation of the HA crosslinked shell by HAase rich in the tumor microenvironment, the changes in the particle size and zeta potential of TRAIL/Dox-Gelipo were monitored after incubation with HAase at pH 6.5 (the typical tumor extracellular pH) over time. As shown in FIG. 16C, the particle size of TRAIL/Dox-Gelipo reduced sharply from 125 nm to 105 nm in the first 5 min, and continuously decreased to 83 nm within 1 h, which was attributed to the degraded small molecular HA fragments shedding from Gelipo. Moreover, After a 1 h incubation with HAase, the surface charge of the Gelipo reversed from −20 mV to +10 mV, suggesting that the HA shell degradation of Gelipo led to the exposure of positively charged R8H3-L, the liposomal core of Gelipo, which plays a significant role in the enhancement on the tumor cellular uptake.[27] More importantly, the degradation of the HA shell by HAase facilitates the release of TRAIL from TRAIL/Dox-Gelipo at the tumor site, which can subsequently bind to the DR on the cellular surface to induce apoptosis. To evaluate the HAase-mediated release of TRAIL, we investigated the in vitro release profile of rhodamine-labeled TRAIL (r-TRAIL) from Gelipo without Dox (r-TRAIL-Gelipo) in the presence and absence of HAase at pH 6.5 at 37° C. As shown in FIG. 16D, only 2.3% of r-TRAIL was released from r-TRAIL-Gelipo in the first 5 min and about 6.8% was released within 1 h in the absence of HAase. In contrast, the presence of HAase accelerated the release of r-TRAIL from r-TRAIL-Gelipo. After incubation with HAase, 20.7% of r-TRAIL was released from r-TRAIL-Gelipo in the first 5 min and more than 50% was released within 1 h. Furthermore, the circular dichroism (CD) spectrum of the released TRAIL was in agreement with that of the native TRAIL (FIG. 23), indicating that there were no noticeable conformational changes in the secondary structure of TRAIL during the process of the assembly and disassembly of Gelipo. Accordingly, it was demonstrated that HAase, rich in the tumor extracellular matrix, can degrade the HA shell of Gelipo, which was determined by the size reduction and charge conversion, thereby promoting the release of TRAIL toward the cellular membrane for initiation of death signaling and simultaneously allowing the exposure of R8H3 for enhanced cellular uptake.

Site-Specific Delivery of TRAIL and Dox by Gelipo.

Figure 17:
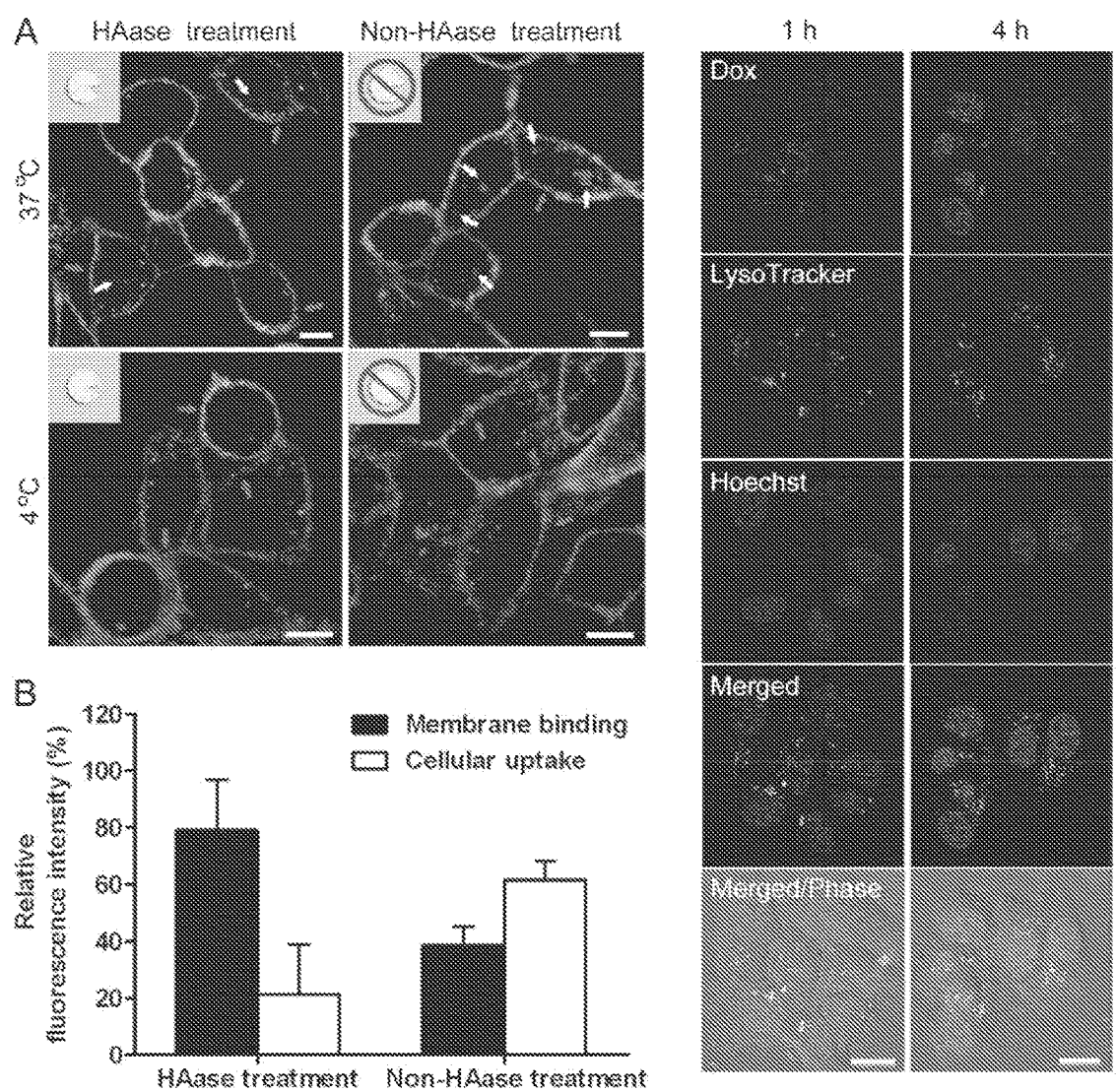
FIG. 17. A) Membrane binding efficiency of r-TRAIL from r-TRAIL-Gelipo with and without 30 min of HAase pre-treatment on MDA-MB-231 cells observed by CLSM. The plasma membranes were stained by Alexa Fluor 488 conjugate of wheat germ agglutinin (WGA). Scale bars are 10 μm. B) Quantitative analysis on the r-TRAIL amount on the plasma membrane and in the cells. C) Intracellular delivery of TRAIL/Dox-Gelipo after 30 min of HAase pre-treatment on MDA-MB-231 cells at different time observed by CLSM. The late endosomes and lysosomes were stained by LysoTracker Green, and the nuclei were stained by Hoechst 33342. Scale bars are 20 μm.

To validate that the released TRAIL from the degraded HA shell of the Gelipo can efficiently bind onto the tumor cellular membrane, the human breast adenocarcinoma (MDA-MB-231) cells were incubated with r-TRAIL-Gelipo with or without HAase pre-treatment at different temperatures for 1 h followed by observation using the confocal laser scanning microscope (CLSM). The endocytosis of the nanoparticle is inhibited at 4° C.,[28] while both the internalization and membrane binding occurred at 37° C. As shown in FIG. 17A, there was a remarkable difference in the distribution of r-TRAIL from r-TRAIL-Gelipo without HAase treatment between at 4° C. and at 37° C. A significantly larger amount of red rhodamine fluorescence was localized onto the green fluorescent cellular membrane than within the cells at 4° C., which implied that the endocytosis of Gelipo was inhibited by lowering the temperature and Gelipo was only able to bind on the plasma membrane. However, at 37° C., most of red rhodamine fluorescence was detected within the cells, indicating that the encapsulated r-TRAIL in Gelipo can be easily transported into the cells via the endocytosis of Gelipo by the cells. In sharp contrast, after 30 min HAase treatment, a great majority of red fluorescence of r-TRAIL was apparently dispersed on the cellular membrane. Furthermore, the quantitative assay substantiated that 80% of r-TRAIL was determined to have bound onto the membrane after HAase treatment, 4-fold that within the cells, whereas without HAase treatment, a higher amount of r-TRAIL in the cells was detected than that on the membrane (FIG. 17B). It was therefore confirmed that the degradation of the HA shell of Gelipo by HAase leads to a rapid release of TRAIL at the tumor site, which can efficiently bind onto the tumor cellular membrane to trigger the following extrinsic apoptosis pathway.

Figure 24:
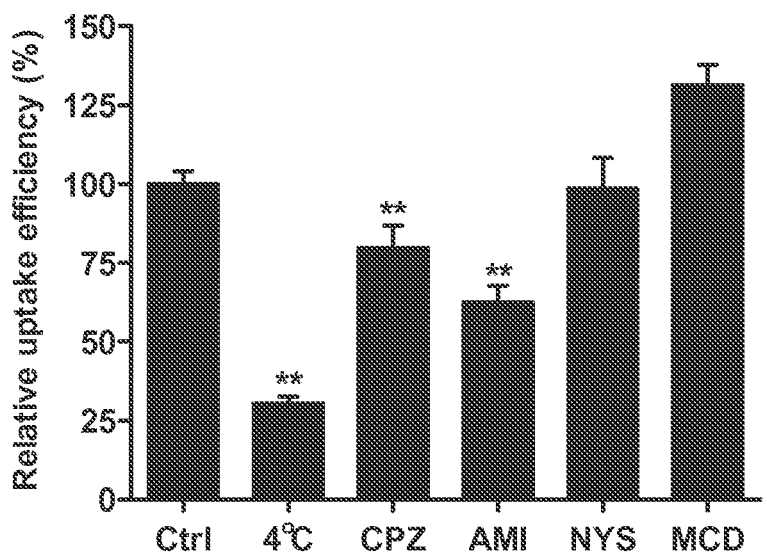
FIG. 24. Relative uptake efficiency of Dox-Gelipo after HAase-treatment on MDA-MB-231 cells in the presence of various endocytosis inhibitors. **P<0.01. Inhibitor of endocytosis: low temperature (4° C.); Inhibitor of clathrin-mediated endocytosis: sucrose (SUC) and chlorpromazine (CPZ); inhibitor of caveolin-mediated endocytosis: nystatin (NYS); inhibitor of macropinocytosis: amiloride (AMI); inhibitor of lipid raft: methyl-β-cyclodextrin (MCD). Compared with the cellular uptake of Dox-Gelipo without inhibitors as a control, the significant decrease in the uptake of Dox-Gelipo with inhibitors demonstrated the corresponding endocytosis pathways of Gelipo.
Figure 25:
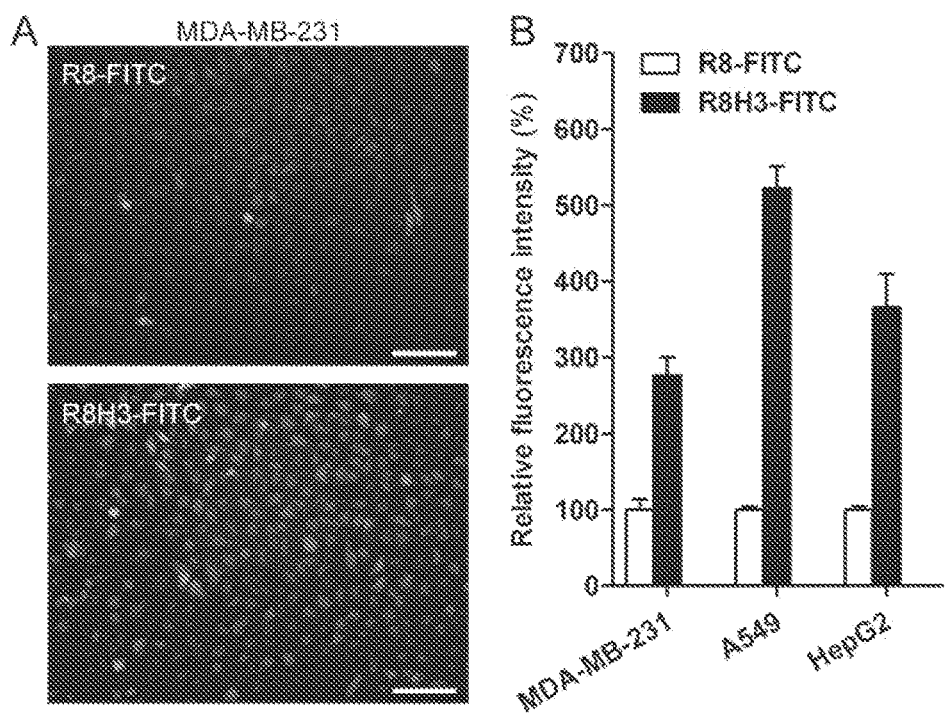
FIG. 25. (A) Fluorescence images of MDA-MB-231 cells incubated with R8-FITC (10 μM) and R8H3-FITC (10 μM) for 1 h. Scale bar are 400 μm. (B) Relative cellular uptake of R8-FITC (10 μM) and R8H3-FITC (10 μM) on MDA-MB-231, A549 and HepG2 cells for 1 h. The cellular uptake of R8H3-FITC was compared with that of R8-FITC, which was normalized as 100%. R8H3-FITC showed higher cell penetrating capability than R8-FITC, which had the cellular uptake of 1.76-fold, 4.23-fold and 2.65-fold increased on MDA-MB-231, A549 and HepG2 cells, respectively.
Figure 26:
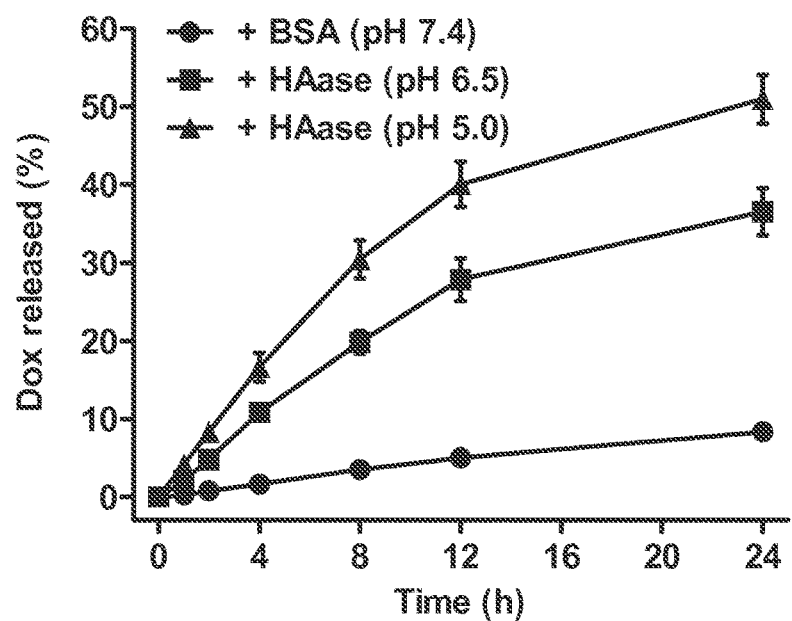
FIG. 26. In vitro release of Dox from Dox-Gelipo at different pH values. BSA was used to simulate the proteins in the blood. Dox-Gelipo showed a good stability in the presence of a high concentration of BSA at pH 7.4, from which only 8% of Dox was released within 24 h, suggesting that the HA shell can protect Gelipo against the attack of the proteins in the blood. In contrast, 36% and 51% of Dox was released from Dox-Gelipo at pH 6.5 and pH 5.0 within 24 h, respectively, indicating that the Dox release was accelerated in the acidic tumor environment and endo-lysosomes with the HA shell degradation by HAase.

Next, the intracellular delivery of TRAIL/Dox-Gelipo after HAase treatment in MDA-MB-231 cells was further investigated using CLSM. Gelipo was demonstrated to be internalized by the cells via a combination of clathrin-dependent endocytosis and macropinocytosis-mediated engulfment (FIG. 24) and subsequent localization into the endosomes and lysosomes.[29] As shown in FIG. 17C, a large number of the endocytosed Gelipo was located in the green fluorescent endo-lysosomes, evidenced by the overlaid yellow fluorescence during the first 1 h of incubation. Nevertheless, after 4 h of incubation, an evident separation of the red fluorescent Gelipo and the green fluorescent endo-lysosomes was observed, which indicated that Gelipo efficiently escaped from the endo-lysosomes with the assistance of R8H3 possessing a high cell penetrating capability (FIG. 25). Of note, the released Dox from Gelipo (FIG. 26) specifically accumulated into the blue fluorescent nuclei judged by the merged magenta fluorescence, which plays an important role in activation of the intrinsic apoptosis pathway. Collectively, Gelipo is able to sequentially release TRAIL and Dox upon the characteristics of the tumor extracellular and intracellular conditions, which can efficiently deliver the released TRAIL and Dox to their distinct sites for anticancer activities.

In Vitro Synergistic Apoptosis and Cytotoxicity.

Figure 18:
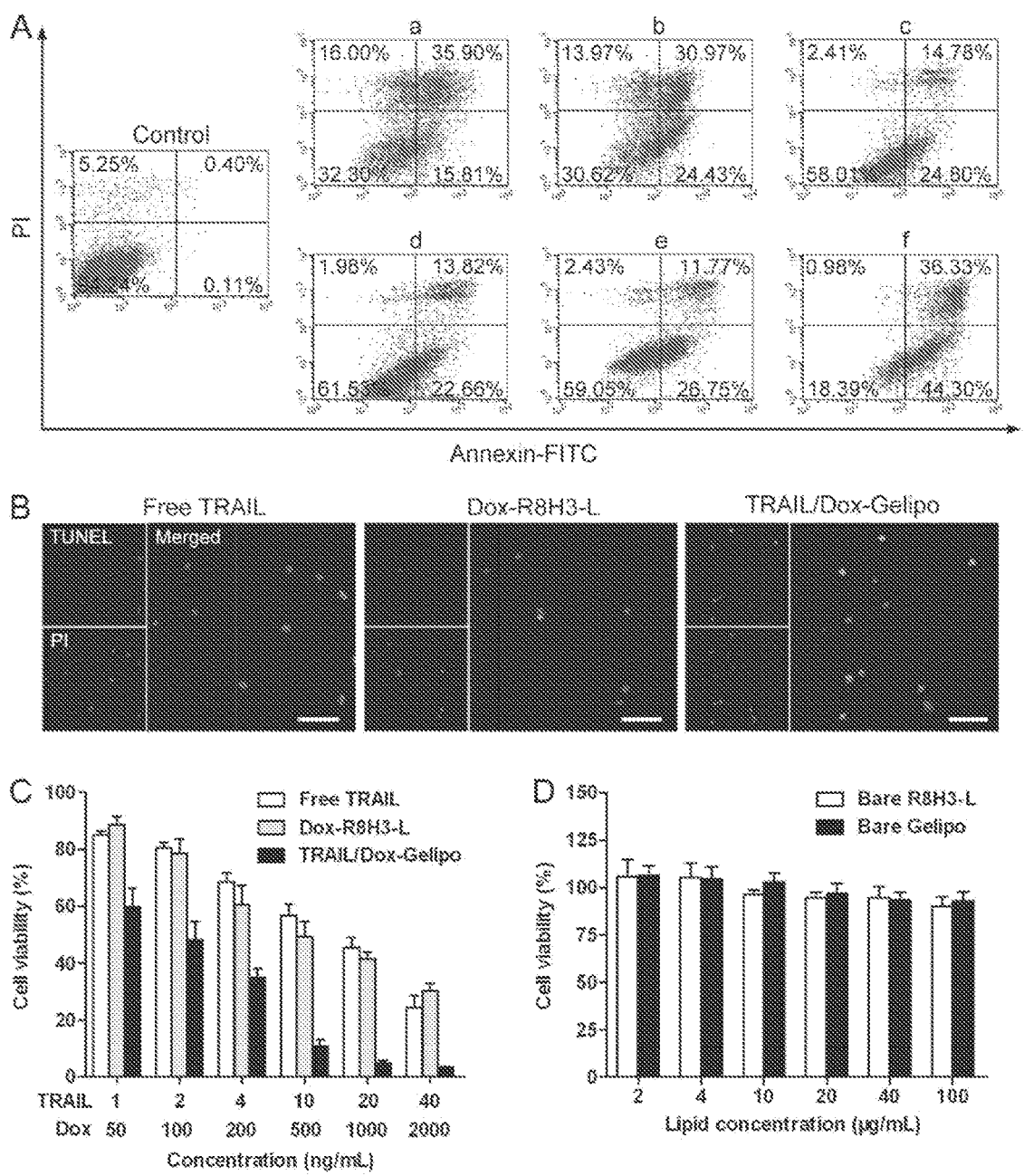
FIG. 18. A) Flow cytometric analysis of MDA-MB-231 cell apoptosis induced by different formulations for 12 h by using Annexin V-FITC/PI staining. a, free TRAIL (20 ng/mL); b, TRAIL-Gelipo (20 ng/mL) after 30 min of HAase pre-treatment; c, TRAIL-Gelipo (20 ng/mL) without HAase pre-treatment; d, free TRAIL (2 ng/mL); e, Dox-R8H3-L (100 ng/mL); TRAIL/Dox-Gelipo (2 ng/mL TRAIL, 100 ng/mL Dox) after 30 min of HAase pre-treatment. B) MDA-MB-231 cell apoptosis induced by free TRAIL (2 ng/mL), Dox-R8H3-L (100 ng/mL) and TRAIL/Dox-Gelipo (2 ng/mL, TRAIL, 100 ng/mL Dox) after a 30 min of HAase pre-treatment for 18 h using the APO-BrdU TUNEL assay. Alexa Fluor 488-stained nick end label showed green fluorescence, and PI-stained nuclei showed red fluorescence. Scale bar is 100 μm. C) In vitro cytotoxicity of free TRAIL, Dox-R8H3-L and TRAIL/Dox-Gelipo toward MDA-MB-231 cells for 24 h. D) In vitro cytotoxicity of the bare R8H3-L and Gelipo toward MDA-MB-231 cells for 24 h.

Based on the site-specific delivery of TRAIL and Dox by Gelipo, the apoptosis-inducing activity of the released TRAIL through the degradation of HA shell of Gelipo was first explored toward MDA-MB-231 cells using the Annexin-FITC apoptosis detection assay. As shown in FIG. 18A, after 12 h of cell incubation, free TRAIL (20 ng/mL) showed a strong capability of inducing apoptosis, which had an apoptosis ratio of 51.71% and a viability of 32.30%. TRAIL-Gelipo without Dox after HAase treatment had an apoptosis-inducing capability comparable to free TRAIL. In contrast, the viability increased to 58.01% and the apoptosis ratio decreased to 39.58% when the cells were incubated with TRAIL-Gelipo without pre-treatment of HAase. It was suggested that HAase-mediated TRAIL release from Gelipo contributed to the distribution of TRAIL onto the membrane similar to that of free TRAIL for maximizing apoptosis activity, whereas without HAase treatment, the endocytosis of Gelipo with the encapsulated TRAIL into the cells relatively reduced the apoptosis-inducing ability of TRAIL.

We then evaluated the synergistic apoptosis-inducing effect of TRAIL and Dox by Gelipo on MDA-MB-231 cells. As shown in FIG. 18A, either free TRAIL (2 ng/mL) or Dox-R8H3-L (100 ng/mL) showed the apoptosis-inducing characteristics, and the apoptosis ratios were 36.48% and 38.52%, respectively. Of note, HAase-treated TRAIL/Dox-Gelipo at a fixed concentration ratio of 2 ng/mL TRAIL and 100 ng/mL Dox had a prominent apoptosis ratio higher than 80%. In addition, assessed by the terminal deoxynucleotidyl transferase dUTP nick end labeling (TUNEL) assay, MDA-MB-231 cells incubated with HAase-treated TRAIL/Dox-Gelipo exhibited broader apoptotic DNA fragmentation stained as green fluorescence compared to that treated with the single therapeutics, free TRAIL or Dox-R8H3-L only (FIG. 18B). These results substantiated that TRAIL/Dox-Gelipo has a synergistic induction of apoptosis toward cancer cells through the combination efficacy of TRAIL and Dox.

Figure 27:
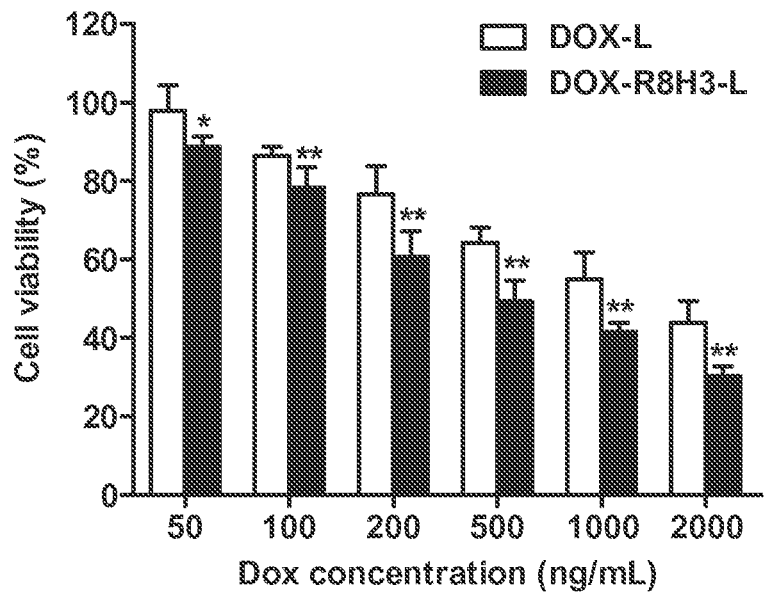
FIG. 27. In vitro cytotoxicity of Dox-L and Dox-R8H3-L on MDA-MB-231 cells for 24 h. *P<0.05, **P<0.01.

The in vitro cytotoxicity of TRAL/Dox-Gelipo against MDA-MB-231 cells was evaluated by using the 3-(4,5-dimethylthiazol-2-yl)-2,5-diphenyitetrazolium bromide (MTT) assay. As shown in FIG. 18C, the half-maximal inhibitory concentration ($IC_{50}$) of Dox-R8H3-L was 542 ng/mL on MDA-MB-231 cells, which was 1.3-fold increase compared to that of Dox-L without R8H3 decoration (FIG. 27), indicating that R8H3 promotes the efficient intracellular delivery of the liposomes. More importantly, TRAIL/Dox-Gelipo after HAase treatment displayed a significantly greater cytotoxicity against MB-MDA-231 cells with the $IC_{50}$ of 86 ng/mL (Dox concentration), Additionally, the bare R8H3-L and Gelipo without TRAIL and Dox showed negligible toxicity within all the tested concentrations (FIG. 18D). Consequently, the combination delivery of TRAIL and Dox to their primary activity sites provides a high potential for improved cytotoxicity.

In Vivo Targetability and Antitumor Efficacy.

Figure 19:
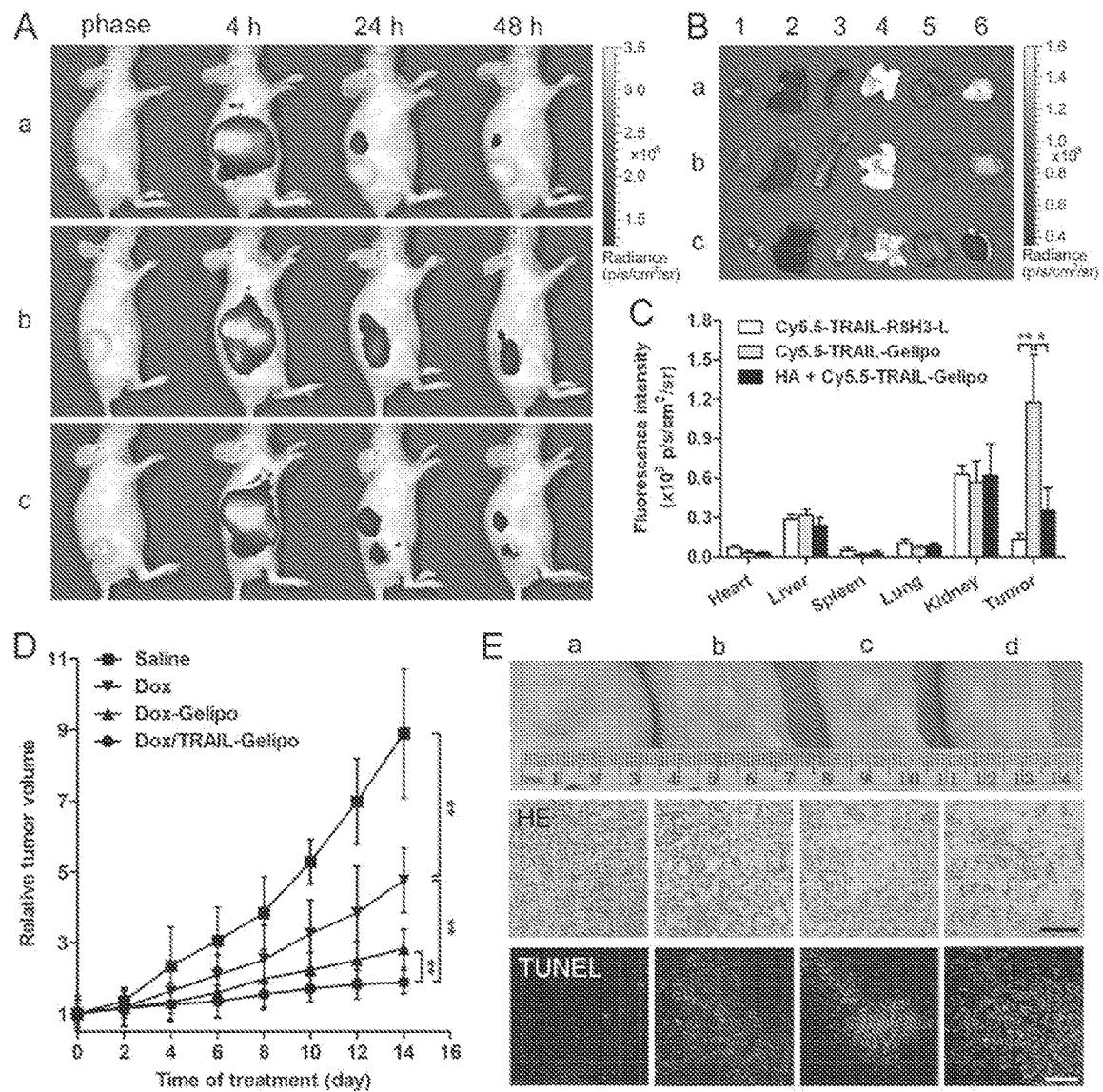
FIG. 19. A) In vivo fluorescence imaging of the MDA-MB-231 tumor-bearing nude mice at 4, 24, and 48 h after intravenous injection of Cy5.5-TRAIL-R8H3-L (a), Cy5.5-TRAIL-Gelipo (b) and Cy5.5-TRAIL-Gelipo with pre-injection of free HA (c) at Cy5.5 dose of 30 nmol/kg. The arrows indicate the regions of the tumors. B) Ex vivo fluorescence imaging of the tumor and normal tissues of the MDA-MB-231 tumor-bearing nude mice after mice were euthanized at 24 h post injection. 1, heart; 2, liver; 3, spleen; 4, lung; 5, kidney; 6, tumor. C) ROI analysis of fluorescent signals from the tumors and normal tissues. *P<0.05, P<0.01. D) The MDA-MB-231 tumor growth curves after intravenous injection of different formulations of Dox at a dose of 2 mg/kg. P<0.01. (E) Representative images of MDA-MB-231 xenograft tumors of the mice after treatment with saline (a), the Dox solution (b), Dox-Gelipo (c) and TRAIL/Dox-Gelipo (d) at Day 14; Histological observation of the tumor tissues after treatment. The tumor sections were stained with HE. Scale bar is 100 μm; Detection of apoptosis in the tumor tissues after treatment. The tumor sections were stained with fluorescein-dUTP (green) for apoptosis and Hoechst for nuclei (blue). Scale bar is 100 μm.

To estimate the targetability of Gelipo in vivo, the biodistribution of Cy5.5-labeled TRAIL (Cy5.5-TRAIL) loaded Gelipo (Cy5.5-TRAIL-Gelipo) administrated intravenously into the MB-MDA-231 tumor-implanted nude mice was monitored by a non-invasive near infrared optical imagining technique. As shown in FIG. 19A, Cy5.5-TRAIL-Gelipo exhibited a stronger Cy5.5 signal at the tumor site at 4 h post-injection. As time extended, a higher fluorescence signal was clearly observed in the tumor region compared with that in the normal tissues within 48 h post-injection, validating the significant tumor targeting effect of Gelipo. However, almost no signal at the tumor site was imaged after a 48 h injection of Cy5.5-TRAIL-R8H3-L without HA coating, which mainly resulted from a rapid clearance of cationic liposomes.[30] To further confirm the role of the HA shell in the active targeting of Gelipo to CD44 overexpressing tumor, a high dose of HA polymer was injected before the administration of Gelipo. As expected, a conspicuous attenuation of Cy5.5 signal at the tumor site was visualized at all the time points, revealing that the HA shell not only retained the stability of Gelipo in the systemic circulation but also endued Gelipo with the active tumor targetability. After 48 h imaging, the tumor and normal tissues were separated from the mice after euthanasia for ex vivo imaging. As shown in FIG. 19B, the strongest Cy5.5 signal was observed at the tumor tissue after applying Cy5.5-TRAIL-Gelipo compared to Cy5.5-TRAIL-R8H3-L and Cy5.5-TRAIL-Gelipo pretreated with HA, and this fluorescence signal was much higher than that at the normal tissues. The quantitative region-of-interest (ROI) analysis determined that Cy5.5-TRAIL-Gelipo had the fluorescence intensity at the tumor site 8.6-fold and 3.4-fold that of Cy5.5-TRAIL-R8H3-L and Cy5.5-TRAIL-Gelipo pretreated with HA, respectively, as well as 2.7-fold and 1.1-fold increase compared to that in the liver and kidney, respectively (FIG. 19C). It was confirmed that Gelipo had a high tumor targetability as a result of a combination of the passive and active targeting mechanisms.

Figure 28:
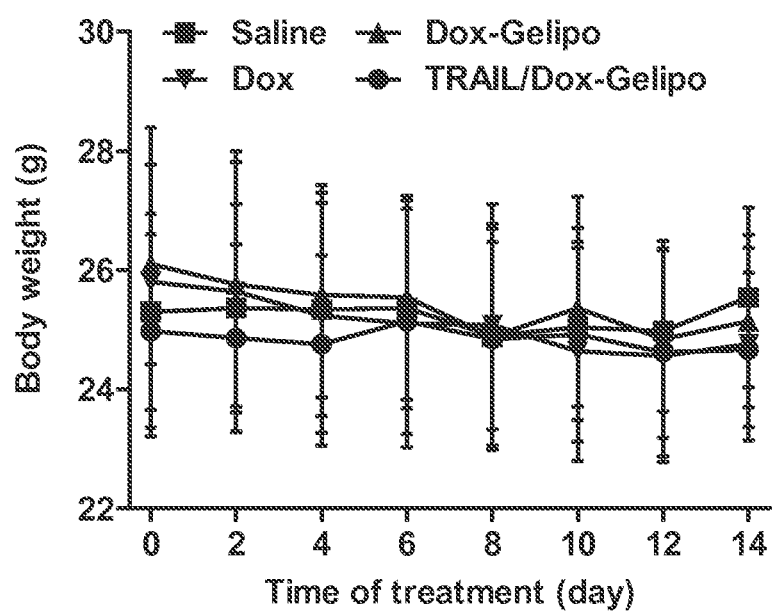
FIG. 28. The body weight change of MDA-MB-231 tumor-bearing mice during treatment.

To demonstrate the feasibility of Gelipo for cancer treatment in vivo, the antitumor activity of Dox/NG was evaluated using MDA-MB-231 tumor xenograft models. As shown in FIG. 19D, the tumor growth was remarkably suppressed after the successive intravenous injection of various Dox formulations including the Dox solution, Dox-loaded Gelipo without TRAIL (Dox-Gelipo) and TRAIL/Dox-Gelipo, compared with saline as a negative control. Dox-Gelipo generated a noticeably higher effect on inhibiting tumor growth than the Dox solution, which mainly resulted from the EPR effect of nanoscaled Gelipo combined with the active targeting capability provided by the HA shell. It is worth noting that TRAIL/Dox-Gelipo showed a dominant effect on tumor inhibition compared with Dox-Gelipo (FIG. 19D, E), further validating the synergistic antitumor effect by a combination of TRAIL and Dox. The body weight of mice receiving TRAIL/Dox-Gelipo remained stable during the treatment (FIG. 28). The histologic images of the tumor section stained by the hematoxylin and eosin (HE) showed a massive cancer cell remission after applying TRAIL/Dox-Gelipo (FIG. 19E), which offered a considerable evidence of the efficient in vivo antitumor activity of TRAIL/Dox-Gelipo. Moreover, the fluorescence images obtained using the in situ TUNEL assay presented the highest level of cell apoptosis in the tumor collected from the mice receiving TRAIL/Dox-Gelipo (FIG. 19E), indicating that the prominent capability of tumor growth inhibition was partly due to the elevated apoptosis activated by TRAIL/Dox-Gelipo. Taken together, it was verified that TRAIL/Dox-Gelipo preferentially accumulated at the tumor site, efficiently delivered the TRAIL and Dox to their specific sites of activity, and thereby accomplished optimal synergistic antitumor efficacy.

Conclusions.

In summary, we successfully developed "Gelipo" with a liposomal core and a crosslinked HA shell for sequential and site-specific delivery (SSSD) of TRAIL and Dox. Gelipo is able to efficiently deliver its cargos, TRAIL and Dox at the tumor sites in a programmed fashion. At the HAase-rich tumor microenvironment, the HA outer corona of Gelipo was degraded by HAase and peeled off, followed by the extracellular release of TRAIL to bind onto the membrane receptor to trigger the extrinsic apoptosis pathway. Meanwhile, the degradation of the HA shell allowed the exposure of R8H3 with a high cellular penetrating ability, which contributed to the enhanced cellular uptake and efficient intracellular delivery of Dox for activation of the intrinsic apoptosis pathway. Gelipo achieved a synergistic antitumor activity by a combined efficacy of TRAIL and Dox. In addition to TRAIL, other proteins that act on the tumor cellular membrane, such as cetuximab[17a] and trastuzumab,[18] could also be loaded in the interspace between the HA shell and the liposomal core and be release by HAase invasion, which provides more opportunities for combination cancer treatment with gene therapy (siRNA, pDNA) or chemotherapy (Dox, Ptx, cisplatin). Our "SSSD" based design strategy will open an avenue for the exploration of more sophisticated DDSs, which can synergistically differentiate the extracellular and intracellular target to promote a superior anticancer effect.

Experimental Section

Materials:

All chemicals unless mentioned were purchased from Sigma-Aldrich. Stearyl R8H3 (R8H3-C18) as well as FITC-labeled R8H3 (R8H3-FITC) and R8 (R8-FITC) were purchased from the GL Biochem Co., Ltd. (Shanghai, China). Sodium hyaluronic acid (HA, the molecular weight of 77 kDa) was purchased from Freda Biochem Co., Ltd. (Shandong, China). Doxorubicin hydrochloride was purchased from BIOTANG Inc. (Lexington, Mass., USA).

Preparation and Characterization of Gel-Liposome (Gelipo):

Dox-loaded liposomes (Dox-L) were prepared by the transmembrane pH gradient method. Egg phosphatidylcholine (EPC) and cholesterol (5:1, w:w) were dissolved in chloroform, followed by rotation vacuum evaporation at 40° C. to form a thin lipid film. After overnight vaccum dry to remove trace organic solvent, the lipid film was hydrated in 200 mM ammonium sulfate ($(NH_4)_2SO_4$), dispersed by a probe-type ultrasonicator and extruded through the filter membranes with the pore size of 0.45 μm and 0.20 μm successively, followed by dialysis overnight. Then, the blank liposomes were mixed with the Dox solution (Dox:lipids, 1:20, w:w) and incubated at 45° C. for 40 min. The resulting Dox-L was obtained by washing with DI water using centrifugal filters (10K MWCO) (Millipore) to remove free Dox. Subsequently, the pre-cold Dox-L was incubated with TRAIL (Dox:TRAIL, 50:1, w:w) at 4° C. for 0.5 h, followed by addition of R8H3-C18 (2.5 mol % of the total lipid weight) and incubation for additional 0.5 h. This solution was then added into the m-HA solution (HA:lipids, 3:20, w:w), followed by adding a crosslinker, N,N-methylenebisacrylamide (MBA) (MBA:m-HA, 1:1, w:w) and a photoinitiator Irgacure 2959 (0.1%, w:v). After radical polymerization via UV radiation for 60 s using a BlueWave 75 UV Curing Spot Lamp (DYMAX), TRAIL and Dox co-loaded Gel-Liposome (TRAIL/Dox-Gelipo) was obtained by washing with HEPES buffer (10 mM, pH 7.4) using centrifugal filters (30K MWCO) (Millipore) to remove the excessive crosslinker and initiator. The particle size and zeta potential of TRAIL/Dox-Gelipo were measured by a Zetasizer (Nano ZS, Malvern). For TEM observation, TRAIL/Dox-Gelipo was dropped onto a TEM copper grid (300 mesh) (Ted Pella) and then stained by phosphotungstic acid (1%, v:v). After air-dry, the sample was observed by TEM (JEM-2000FX, Hitachi) operating at 80 kV.

Degradation of HA Shell:

500 μL of Gelipo was incubated with 500 μL of HAase (1 mg/mL) at pH 6.5 in a 37° C. water bath. At predetermined time intervals, the particle size and zeta potential of the samples were immediately measured by a Zetasizer (Nano ZS, Malvern).

In Vitro HAase-Mediated TRAIL Release:

500 μL of rhodamine-labeled TRAIL-loaded Gelipo (r-TRAIL-Gelipo) was incubated with 500 μL of HAase (1 mg/mL) at pH 6.5 in a 37° C. water bath. At prearranged time intervals, free r-TRAIL in the filtrate was harvested using centrifugal filters (30K MWCO) (Millipore). The fluorescence intensity of r-TRAIL was determined at 585 nm with an excitation wavelength of 552 nm by a microplate reader (Infinite M200 PRO, Tecan). Additionally, the far-UV CD spectra of the native TRAIL and the released TRAIL from TRAIL Gelipo were obtained using a Circular Dichroism Spectrometer (Aviv).

Cell Culture:

MDA-MB-231 cells were cultured in DMEM containing FBS (10%, v:v), penicillin (100 U/mL) and streptomycin (100 μg/mL) in an incubator (Thermo Scientific) at 37° C. under an atmosphere of 5% $CO_2$ and 90% relative humidity. The cells were sub-cultivated approximately every 3 days at 80% confluence using trypsin (0.25%, w:v) at a split ratio of 1:5.

Site Specific Delivery:

MDA-MB-231 cells ($1 \times 10^5$ cells/well) were seeded in a confocal microscopy dish (MatTek) and cultured for 24 h. For the membrane binding assay, the cells were incubated with r-TRAIL-Gelipo (0.2 μg/mL) treated with HAase (1 mg/mL) for 30 min, at 37° C. or 4° C. for 1 h. Afterwards, the cells were washed with ice-cold PBS twice, and stained by Alexa Fluor 488 conjugate of WGA Green (5 μg/mL) (Life Technologies) at 37° C. for 10 min. The cells were washed with ice-cold PBS twice, and immediately observed using confocal laser scanning microscope (CLSM) (LSM710, Zeiss).

For quantitative analysis, the cells were incubated with r-TRAIL-Gelipo (0.2 μg/mL) with or without HAase-treatment at 37° C. or 4° C. for 1 h. The cells were harvested and washed by ice-cold PBS thrice. The fluorescence intensity of r-TRAIL was measured at 585 nm with an excitation wavelength of 552 nm, which was normalized by subtracting the background signal of the blank cells. The cell proteins were assayed by the Pierce BCA protein assay kit (Thermo Scientific). The amount of r-TRAIL binding on the plasma membrane or internalized within the cells ($U_{r\text{-}TRAIL}$) was calculated as: $U_{r\text{-}TRAIL}$ (ng/mg)=$Q_{r\text{-}TRAIL}/Q_{protein}$, where $Q_{r\text{-}TRAIL}$ and $Q_{protein}$ were the amounts of r-TRAIL and cellular protein, respectively. $U_{r\text{-}TRAIL}$ after incubation at 37° C. indicated the total amount of r-TRAIL binding on the plasma membrane plus internalized within the cells, while that after incubation at 4° C. referred to the amount of TRAIL binding on the plasma membrane due to the endocytosis inhibition at 4° C.

For the intracellular delivery study, the cells were incubated with Dox-Gelipo (1 μg/mL) after HAase-treatment at 37° C. for 1 h and 4 h. Then, the cells were washed with ice-cold PBS twice, and stained by LyosTracker Green (50 nM) (Life Technologies) at 37° C. for 30 min and Hoechst 33342 (1 μg/mL) (Life Technologies) at 37° C. for 10 min. The cells were washed by ice-cold PBS twice and immediately observed using CLSM (LSM710, Zeiss).

In Vitro Cytotoxicity:

MDA-MB-231 ($1 \times 10^4$ cells/well) were seeded in 96-well plates and cultured for 24 h. The cells were exposed to free TRAIL, Dox-R8H3-L and TRAIL/Dox-Gelipo (TRAIL: Dox, 1:50, w:w) after the HAase treatment at different concentrations of Dox for 24 h. 20 μL of the MTT solution (5 mg/mL) was added into each well and the cells was stained for 4 h. Then the medium was removed, and the cells were dissolved in 150 μL of dimethyl sulfoxide (DMSO). The absorbance was measured at a test wavelength of 570 nm and a reference wavelength of 630 nm by a microplate reader (Infinite M200 PRO, Tecan).

Cell Apoptosis Assay:

Apoptosis of MDA-MB-231 cells was detected using the Annexin V-FITC Apoptosis Detection Kit (BD Biosciences) and APO-BrdU TUNEL Assay Kit (Life Technologies), respectively. The cells ($1\times10^5$ cells/well) were seeded in 6-well plates and cultured for 48 h. For Annexin V-FITC assay, the cells were incubated with different formulations for 12 h, including free TRAIL (2 or 20 ng/mL), TRAIL-Gelipo (20 ng/mL) with or without HAase-treatment, Dox-R8H3-L (100 ng/mL), TRAIL/Dox-Gelipo (2 ng/mL TRAIL, 100 ng/mL Dox) with HAase-treatment. For TUNEL assay, the cells were incubated with free TRAIL (2 ng/mL), Dox-R8H3-L (100 ng/mL) and TRAIL/Dox-Gelipo (2 ng/mL TRAIL, 100 ng/mL Dox) with HAase-treatment for 20 h, respectively. The following procedures were performed in accordance with the manufacturers' protocols. Finally, for Annexin V-FITC assay, the cells were analyzed by flow cytometry (BD FACSCalibur), while for TUNEL assay, the cells were observed by fluorescence microscope (IX71, Olympus).

Animals and Tumor Xenograft Models:

All animals were treated in accordance with the Guide for Care and Use of Laboratory Animals, approved by local committee. The female nude mice were subcutaneously inoculated in the back with MDA-MB-231 cells ($1\times10^7$ cells/mouse) for the construction of the tumor xenograft model. The tumor size was monitored by a fine caliper and the tumor volume (V) was calculated as $V=L\times W^2/2$, where L and W were the length and width of the tumor, respectively.

In Viva Imaging Study:

When the tumors reached to 200-400 mm$^3$, the mice were intravenously injected by Cy5.5-TRAIL-R8H3-L and Cy5.5-TRAIL-Gelipo at Cy5.5 dose of 30 nmol/kg, respectively. For HA competitive study, the mice were injected by Cy5.5-TRAIL-Gelipo at 30 min after pre-injected by a high dose of free HA (50 mg/kg). Images were taken on IVIS Lumina imaging system (Caliper, USA) at 4, 24 and 48 h post injection. After the 48 h imaging, the tumors as well as major organs were collected from the mice after euthanasia and subjected for ex vivo imaging. ROIs were circled around the organs, and the fluorescence intensities were analyzed by Living Image Software.

In Vivo Antitumor Efficacy:

When the tumor volume reached to 50 mm$^3$, the mice were weighed, randomly divided into 4 groups, and intravenously administered with the Dox solution (2 mg/kg), Dox-Gelipo (2 mg/kg), Dox/TRAIL-Gelipo (2 mg/kg Dox, 0.04 mg/kg TRAIL) and saline every other day for 12 days. The tumor size and body weight of the mice were measured at the meantime. At Day 14, the tumor were harvested from the mice after euthanasia, washed by saline thrice and then fixed in 10% neutral buffered formalin (NBF). For HE staining, formalin-fixed tumors were embedded in paraffin blocks and visualized by optical microscope (DM5500B, Leica). For TUNEL apoptosis staining, the fixed tumor sections were stained by the In Situ Cell Death Detection Kit (Roche Applied Science) according to the manufacturer's protocol. Hoechst 33342 was used for nuclear nuclear counterstaining. The stained tumor slides were observed by fluorescence microscope (IX71, Olympus).

Statistical Analysis: Data are given as mean± standard deviation. Statistical significance was tested by two-tailed Student's t-test or one-way ANOVA. Statistical significance was set at *P<0.05, and extreme significance was set at **P<0.01.

EXAMPLE 2 REFERENCES

[1] a) J. Bergh, I. M. Bondarenko, M. R. Lichinitser, A. Liljegren, R. Greil, N. L. Voytko, A. N. Makhson, J. Cortes, A. Lortholary, J. Bischoff, A. Chan, S. Delaloge, X. Huang, K. A. Kern, C. Giorgetti, *J. Clin. Oncol.* 2012, 30, 921; b) B. J. Giantonio, P. J. Catalano, N. J. Meropol, P. J. O'Dwyer, E. P. Mitchell, S. R. Alberts, M. A. Schwartz, A. B. Benson, *J. Clin. Oncol.* 2007, 25, 1539; c) W. J. Gradishar, L. A. Meza, B. Amin, D. Samid, T. Hill, Y.-M. Chen, E. E. Lower, P. K. Marcom, *J. Clin. Oncol.* 2004, 22, 2321.

[2] a) J. Lehar, A. S. Krueger, W. Avery, A. M. Heilbut, L. M. Johansen, E. R. Price, R. J. Rickles, G. F. Short, J. E. Staunton, X. W. Jin, M. S. Lee, G. R. Zimmermann, A. A. Borisy, *Nat. Biotechnol.* 2009, 27, 659; b) C. M. Hu, S. Aryal, L. Zhang, *Ther Deliv.* 2010, 1, 323.

[3] a) N. Kolishetti, S. Dhar, P. M. Valencia, L. Q. Lin, R. Karnik, S. J. Lippard, R. Langer, O. C. Farokhzad, *Proc. Natl. Acad. Sci. U.S.A.* 2010, 107, 17939; b) X. B. Xiong, A. Lavasanifar, *ACS Nano* 2011, 5, 5202; c) S. Aryal, C. M. J. Hu, L. F. Zhang, *Small* 2010, 6, 1442.

[4] R. J. Lee, Mol. *Cancer Ther.* 2006, 5, 1639.

[5] a) Y. Liu, J. Du, M. Yan, M. Y. Lau, J. Hu, H. Han, O.O. Yang, S. Liang, W. Wei, H. Wang, J. Li, X. Zhu, L. Shi, W. Chen, C. Ji, Y. Lu, *Nat. Nanotechnol.* 2013, 8, 187; b) Z. Chen, M. F. Penet, S. Nimmagadda, C. Li, S. R. Banerjee, P. T. Winnard, D. Artemov, K. Glunde, M. G. Pomper, Z. M. Bhujwalla, ACS Nano 2012, 6, 7752; c) S. X. Huang, K. Shao, Y. Liu, Y. Y. Kuang, J. F. Li, S. An, Y. B. Guo, H. J. Ma, C. Jiang, *ACS Nano* 2013, 7, 2860.

[6] a) H. Meng, W. X. Mai, H. Y. Zhang, M. Xue, T. Xia, S. J. Lin, X. Wang, Y. Zhao, Z. X. Ji, J. I. Zink, A. E. Nel, *ACS Nano* 2013, 7, 994; b) Y. Chen, Y. Gao, H. Chen, D. Zeng, Y. Li, Y. Zheng, F. Li, X. Ji, X. Wang, F. Chen, Q. He, L. Zhang, J. Shi, *Adv. Funct. Mater.* 2012, 22, 1586; c) C. Wang, H. Xu, C. Liang, Y. Liu, Z. Li, G. Yang, L. Cheng, Y. Li, Z. Liu, *ACS Nano* 2013, 7, 6782.

[7] H. Wang, Y. Zhao, Y. Wu, Y. L. Hu, K. H. Nan, G. J. Nie, H. Chen, *Biomaterials* 2011, 32, 8281.

[8] H. Lataste, V. Senilh, M. Wright, D. Guenard, P. Potier, *Proc. Natl. Acad. Sci. U.S.A.* 1984, 81, 4090.

[9] A. Bodley, L. F. Liu, M. Israel, R. Seshadri, Y. Koseki, F. C. Giuliani, S. Kirschenbaum, R. Silber, M. Potmesil, *Cancer Res.* 1989, 49, 5969.

[10] a) G. Dranoff, *Nat. Rev. Cancer* 2004, 4, 11; b) R. W. Johnstone, A. J. Frew, M. J. Smyth, *Nat. Rev. Cancer* 2008, 8, 782; c) S. Mocellin, C. R. Rossi, P. Pilati, D. Nitti, *Cytokine Growth Factor Rev.* 2005, 16, 35.

[11] a) G. P. Adams, L. M. Weiner, *Nat. Biotechnol.* 2005, 23, 1147; b) A. M. Scott, J. D. Wolchok, L. S. Old, *Nat. Rev. Cancer* 2012, 12, 278.

[12] A. Phelan, G. Elliott, P. O'Hare, *Nat. Biotechnol.* 1998, 16, 440.

[13] A. M. Scott, J. P. Allison, J. D. Wolchok, *Cancer Immun.* 2012, 12, 14.

[14] R. M. Kluck, E. BossyWetzel, D. R. Green, D. D. Newmeyer, *Science* 1997, 275, 1132.

[15] S. A. Lakhani, A. Masud, K. Kuida, G. A. Porter, Jr., C. J. Booth, W. Z. Mehal, I. Inayat, R. A. Flavell, *Science* 2006, 311, 847.

[16] S. W. Lowe, E. Cepero, G. Evan, *Nature* 2004, 432, 307.
[17] aS. Q. Li, K. R. Schmitz, P. D. Jeffrey, J. J. W. Wiltzius, P. Kussie, K. M. Ferguson, *Cancer Cell* 2005, 7, 301; bN. E. Hynes, H. A. Lane, *Nat. Rev. Cancer* 2005, 5, 341.
[18] R. Nahta, M. C. Hung, F. J. Esteva, *Cancer Res.* 2004, 64, 2343.
[19] M. M. Keane, S. A. Ettenberg, M. M. Nau, E. K. Russell, S. Lipkowitz, *Cancer Res.* 1999, 59, 734.
[20] Z. Gu, A, Biswas, M. X. Zhao, Y. Tang, *Chem. Soc. Rev.* 2011, 40, 3638.
[21] a) B. P. Toole, *Nat. Rev. Cancer* 2004, 4, 528; b) E. Kim, J. Yang, J. Park, S. Kim, N. H. Kim, 3.1. Yook, S. S. Suh, S. Haam, Y. M. Huh, *ACS Nano* 2012, 6, 8525.
[22] a) R. Stern, M. J. Jedrzejas, *Chem. Rev.* 2006, 106, 818; b) P. Bertrand, N. Girard, C. Duval, J. d'Anjou, C. Chauzy, J. F. Menard, B. Delpech, *Int. J. Cancer* 1997, 73, 327.
[23] Z. P. Zhen, W. Tang, H. M. Chen, X. Lin, T. Todd, G. Wang, T. Cowger, X. Y. Chen, J. Xie, ACS Nano 2013, 7, 4830.
[24] G. Haran, R. Cohen, L. K. Bar, Y. Barenholz, *Biochim. Biophys. Acta.* 1993, 1151, 201.
[25] I. A. Khalil, K. Kogure, S. Futaki, S. Hama, H. Akita, M. Ueno, H. Kishida, M. Kudoh, Y. Mishina, K. Kataoka, M. Yamada, H. Harashima, *Gene Ther.* 2007, 14, 682.
[26] Z. Gu, M. Yan, B. Hu, K. I. Joo, A. Biswas, Y. Huang, Y. Lu, P. Wang, Y. Tang, *Nano Lett.* 2009, 9, 4533.
[27] a) V. P. Torchilin, R. Rammohan, V. Weissig, T. S. Levchenko, *Proc. Natl. Acad. Sci. U.S.A.* 2001, 98, 8786; b) S. Futaki, T. Suzuki, W. Ohashi, T. Yagami, S. Tanaka, K. Ueda, Y. Sugiura, *J Biol. Chem.* 2001, 276, 5836.
[28] C. E. Ashley, E. C. Carnes, G. K. Phillips, D. Padilla, P. N. Durfee, P. A. Brown, T. N. Hanna, J. Liu, B. Phillips, M. B. Carter, N. J. Carroll, X. Jiang, D. R. Dunphy, C. L. Willman, D. N. Petsev, D. G. Evans, A. N. Parikh, B. Chackerian, W. Wharton, D. S. Peabody, C. J. Brinker, *Nat. Mater.* 2011, 10, 389.
[29] a) G. J. Doherty, H. T. McMahon, *Annu. Rev. Biochem.* 2009, 78, 857; b) R. Mo, Q. Sun, J. Xue, N. Li, W. Li, C. Zhang, Q. Ping, *Adv. Mater.* 2012, 24, 3659-3665; c) R. Mo, Q. Sun, N. Li, C. Zhang, *Biomaterials* 2013, 34, 2773.
[30] R. B. Campbell, D. Fukumura, E. B. Brown, L. M. Mazzola, Y. Izumi, R. K. Jain, V. P. Torchilin, L. L. Munn, *Cancer Res.* 2002, 62, 6831.

EXAMPLE 2 SUPPLEMENTAL INFORMATION

Materials and Methods

Expression of TRAIL. His-ILZ-TRAIL (residues 114-281) (designated TRAIL) was produced in *Escherichia coli* (*E. coli*) by the pET23dw-His-ILZ-hTRAIL vector (a generous gift from Dr. Seulki Lee at the Johns Hopkins School of Medicine). *E. coli* was amplified to mid-log phase and TRAIL expression was induced by the addition of 1 mM isopropylthio-β-galactoside (IPTG) at 20° C. for 12 h. The cells were harvested, resuspended in the lysis buffer, and lysed by a gentle sonication. After centrifugation at 12000×g at 4° C. for 30 min, the supernatant was applied to the Nickle Affinity chromatography, and then purified by elution using the imidazole Tris-HCI buffer solutions at concentration gradient from 10, 20 mM to 250 mM. Finally, a concentrated TRAIL solution was obtained after the buffer exchange with PBS twice by ultracentrifugation. The molecular weight of the obtained TRAIL was determined using the sodium dodecyl sulfate polyacrylamide gel electrophoresis (SDS-PAGE). TRAIL showed about 24 kDa molecular mass in agreement with the previous report.[1]

Synthesis and Characterization of Methacrylated HA (m-HA).

HA was modified with double bond by reacting with the methacrylic anhydride (MA).[2] Two grams of HA was dissolved in 100 mL of distilled (DI) water with stirring in cold room overnight, followed by the addition of 1.6 mL of MA into the HA solution. The pH of the reaction was maintained between 8 and 9 by adding 5N NaOH and kept at 4° C. under continuous stirring for 24 h. Subsequently, m-HA was precipitated in acetone, washed with ethanol and then dissolved in DI water. After dialysis against DI water for 48 h, the purified m-HA was obtained with a yield of 87.5% by lyophilization and characterized by $^1$H NMR (Varian Gemini 2300). The degree of modification (DM) was determined to be about 15% by comparing the ratio of the areas under the proton peaks at 5.74 and 6.17 ppm (methacrylate protons) to the peak at 1.99 ppm (N-acetyl glucosamine of HA) after performing a standard deconvolution algorithm to separate closely spaced peaks.

m-HA: $^1$H NMR (D$_2$O, 300 MHz, 8 ppm): 1.85-1.96 (m, 3H, CH$_2$=C(CH$_3$)CO), 1.99 (s, 311, NHCOCH$_3$), 5.74 (s, 1H, CH$^1$H$^2$=C(CH$_3$)CO), 6.17 (s, 1H, CH$^1$H$^2$=C(CH$_3$) CO).

Synthesis of Rhodamine or Cy5.5 Labeled TRAIL.

2 mg of TRAIL in 2 mL of the sodium carbonate buffer (NaHCO$_3$, 50 mM, pH 8.5) was reacted with 1 mg of rhodamine NHS ester (rhodamine-NHS) (Thermo Scientific) or Cy5.5 NHS ester (Cy5.5-NHS) (KeraFAST) in 50 μL of dimethyl sulphoxide (DMSO) overnight at 4° C. The resulting rhodamine labeled (r-TRAIL) or Cy5.5 labeled TRAIL (Cy5.5-TRAIL) was obtained by washing with PBS using centrifugal filters (3K MWCO) (Millipore) to remove the excessive rhodamine-NHS or Cy5.5-NHS. The fluorescence intensity of r-TRAIL and Cy5.5-TRAIL were detected at an excitation/emission wavelength of 552/585 nm and 673/707 nm by a microplate reader (Infinite M200 PRO, Tecan), respectively.

In Vitro pH-Sensitive Dox Release.

0.5 mL of Dox-Gelipo with the Dox amount of 30 μg in the presence of bovine serum albumin (BSA) (10 mg/mL) or HAase (1 mg/mL) was added into a dialysis tube (10K MWCO) (Slide-A-Lyzer, Thermo Scientific) against 14 mL of the release medium and gently shaken at 37° C. in a shaker (New Brunswick Scientific) at 100 rpm. BSA was used to simulate the proteins in the blood. The release medium was HEPES (10 mM, pH 7.4) or acetate buffer (10 mM, pH 6.5 or pH 5.0). At predetermined time intervals, 0.8 mL of sample was withdrawn, followed by replacing 14 mL of 37° C. fresh buffer solution. The fluorescence intensity of Dox released was measured at an excitation/emission wavelength of 480/596 nm by a microplate reader (Infinite M200 PRO, Tecan).

Determination of Endocytosis Pathways.

MDA-MB-231 (1×10$^5$ cells/well) were seeded in 6-well plates and cultured for 48 h. The cells were pre-incubated with different specific inhibitors for various kinds of endocytosis for 1 h at 37° C., respectively, such as chlorpromazine[3] (CPZ, 10 μM) for the clathrin-mediated endocytosis inhibition, nystatin[4] (NYS, 25 μg/mL) for the caveolin-mediated endocytosis inhibition, amiloride[5] (AMI, 1 mM) for the macropinocytosis inhibition, methyl-β-cyclodextrin [6] (MCD, 3 mM) for the lipid raft inhibition. Subsequently, the cells were incubated with Dox-Gelipo (1 μg/mL) after a 30 min of HAase-treatment (1 mg/mL) in the presence of inhibitors at 37° C. for another 2 h. After washing the cells by ice-cold PBS twice, the fluorescence intensity of Dox in the cells was measured at 595 nm with an excitation wavelength of 480 nm, which was normalized by subtracting the background signal of the blank cells. The cell proteins were assayed by the Pierce BCA protein assay kit (Thermo Scientific). Uptake of Dox ($U_{Dox}$) was calculated as: $U_{Dox}$ (ng/mg)=$Q_{dox}/Q_{protein}$, where $Q_{Dox}$ and $Q_{protein}$ were the amounts of Dox and cellular protein, respectively.

EXAMPLE 2 SUPPLEMENTAL REFERENCES

[1] Y. Youn, M. Shin, S. Chae, C. Jin, T. Kim, K. Lee, *Biotechnol. Lett.* 2007, 29, 713.
[2] E. Hachet, H. Van Den Berghe, E. Bayma, M. Block, R. Auzely-Velty, *Biomacromolecules* 2012, 13, 1818.
[3] X. Zhang, P. Allen, M. Grinstaff, *Mol. Pharmaceutics* 2011, 8, 7584.
[4] Z. ur Rehman, D. Hoekstra, I. Zuhorn, *J. Controlled Release* 2011, 156, 76.
[5] M. Koivusalo, C. Welch, H. Hayashi, C. Scott, M. Kim, T. Alexander, N. Touret, K. Halm, S. Grinstein, *J. Cell Biol.* 2010, 188, 547.
[6] Y. Chiu, Y. Ho, Y. Chen, S. Peng, C. Ke, K. Chen, F. Mi, H. Sung, *J. Controlled Release* 2010, 146, 152.

The foregoing is illustrative of the present invention, and is not to be construed as limiting thereof. The invention is defined by the following claims, with equivalents of the claims included therein.

That which is claimed is:

1. A construct for selectively delivering a compound of interest to a cell, comprising:
   (a) a bioresorbable polymer shell;
   (b) a nucleic acid duplex contained in said shell, said duplex comprising (i) an ATP binding nucleic acid, and (ii) a complementary nucleic acid hybridized to said ATP binding nucleic acid;
   (c) a compound of interest intercalated in or caged by said nucleic acid duplex;
   (d) optionally, a cationic polymer in said bioresorbable polymer shell; and
   (e) optionally, a cell targeting ligand coupled to said polymer shell;
   wherein said polymer shell is degraded in a cell of interest, or in the extracellular matrix of a tissue carrying said cell of interest, to release said duplex therein; and wherein said duplex is destabilized by binding of ATP in said cell of interest to release said compound of interest therein.

2. The construct of claim 1, wherein said bioresorbable polymer shell comprises a crosslinked polymer or copolymer of a polyacrylic acid, polymethacrylic acid, polyethylene amine, a polysaccharide, alginic acid, a pectinic acid, carboxy methyl cellulose, hyaluronic acid, heparin, chitosan, carboxymethyl chitosan, carboxymethyl starch, carboxymethyl dextran, heparin sulfate, chondroitin sulfate, cationic starch, or salts thereof.

3. The construct of claim 1, wherein said bioresorbable polymer shell has an average diameter of from 1 or 10 nanometers to 500 or 1000 nanometers.

4. The construct of claim 1, wherein said ATP binding nucleic acid comprises an ATP binding aptamer.

5. The construct of claim 1, wherein said complementary nucleic acid comprises DNA.

6. The construct of claim 1, wherein said compound of interest is a detectable compound or a cytotoxic compound.

7. The construct of claim 1, wherein said compound of interest comprises a DNA intercalating agent.

8. The construct of claim 7, wherein said DNA intercalating agent comprises doxorubicin, daunorubicin, epirubicin, idarubicin, valrubicine, mitoxantrone, or a combination thereof.

9. The construct of claim 1, wherein said cationic polymer is present.

10. The construct of claim 1, wherein said cell-targeting ligand is present.

11. A composition comprising a construct of claim 1 in a pharmaceutically acceptable carrier.

12. A method of delivering a compound of interest to a cell, comprising the steps of:
    (a) providing a construct of claim 1; and
    (b) contacting said construct to said cell or a tissue carrying said cell, under conditions in which said compound of interest is released therefrom.

13. The method of claim 12, wherein said cell or tissue comprises mammalian cell or tissue.

14. The method of claim 12, wherein said contacting step is carried out in vitro.

15. The method of claim 12, wherein said contacting step is carried out in vivo.

16. A method of treating cancer in a subject in need thereof, comprising administering said subject a construct of claim 1 in a treatment effective amount, wherein said compound of interest comprises an anticancer or antineoplastic agent.

17. The method of claim 16, wherein said cancer is lung, skin, prostate, breast, ovarian, endometrial, colorectal, pancreatic, kidney, bladder, liver, or brain cancer, or leukemia or lymphoma.

* * * * *

UNITED STATES PATENT AND TRADEMARK OFFICE
CERTIFICATE OF CORRECTION

PATENT NO. : 9,919,002 B2
APPLICATION NO. : 15/031151
DATED : March 20, 2018
INVENTOR(S) : Gu et al.

It is certified that error appears in the above-identified patent and that said Letters Patent is hereby corrected as shown below:

In the Specification

Column 23, Line 8: Please correct "40 ΞL" to read -- 40 µL --

Column 23, Line 34: Please correct "8 ppm" to read -- δ ppm --

Column 36, Line 22: Please correct "8 ppm" to read -- δ ppm --

Column 36, Line 23: Please correct "311" to read -- 3H --

Signed and Sealed this
Thirty-first Day of July, 2018

Andrei Iancu
*Director of the United States Patent and Trademark Office*